US006607748B1

United States Patent
Lenaerts et al.

(10) Patent No.: US 6,607,748 B1
(45) Date of Patent: Aug. 19, 2003

(54) CROSS-LINKED HIGH AMYLOSE STARCH FOR USE IN CONTROLLED-RELEASE PHARMACEUTICAL FORMULATIONS AND PROCESSES FOR ITS MANUFACTURE

(76) Inventors: Vincent Lenaerts, 3650 Cote-Saint-Luc, Montreal (Quebec) (CA); Roland Herwig Friedrich Beck, 2501 Blue Mound Dr., Valparaiso, IN (US) 46383; Elsie Van Bogaert, Nieuwstraat 17,2, B-2880 Bornem (BE); Francois Chouinard, 14, chemin d'Aigremont, Lorriane (Quebec) (CA); Reiner Höpcke, Kahle Plack 14, D-47533 Kleve (DE); Cyril Désévaux, 3862 rue des Pâquerettes, Saint-Hubert (Quebec) (CA), J3Y 9A2

( * ) Notice: Subject to any disclaimer, the term of this patent is extended or adjusted under 35 U.S.C. 154(b) by 0 days.

(21) Appl. No.: 09/606,399

(22) Filed: Jun. 29, 2000

(51) Int. Cl.⁷ .............................. A61K 9/20; A61K 9/22; A61K 9/14
(52) U.S. Cl. ...................... 424/464; 424/468; 424/489; 424/488
(58) Field of Search ................................ 424/464, 468, 424/489, 488, 422

(56) References Cited

U.S. PATENT DOCUMENTS

| 2,938,901 A | 5/1960 | Kerr et al. |
| 2,987,445 A | 6/1961 | Levesque |
| 3,034,911 A | 5/1962 | McKee et al. |

(List continued on next page.)

FOREIGN PATENT DOCUMENTS

| EP | 0 499 648 A1 | 8/1992 |
| WO | WO 94/02121 | 2/1994 |
| WO | WO 94/21236 | 9/1994 |
| WO | WO 98/35992 | 8/1998 |

OTHER PUBLICATIONS

Dumoulin, et al., "Cross–Linked Amylose: Enzymatically Controlled Drug Release (ECDR) System", *1993, Proceed. Intern. Symp. Control Rel. Bioact. Mater.*, 20 (1983) 306–307.

Herman, et al., "Modified starches as hydrophilic matrices for controlled oral delivery", *International Journal of Pharmaceutics* 56 (1989) 51–63.

Kost, et al., "Chemically–modified polysaccharide for enymatically–controlled oral drug delivery", *Biomaterials*, 11 (Nov. 1990) 695–698.

V. Lenaerts, et al., "Cross–linked high amylose starch for controlled release of drugs: recent advances", *Journal of Controlled Release* 53 (1998) 225–234.

(List continued on next page.)

*Primary Examiner*—Thurman K. Page
*Assistant Examiner*—Blessing Fubara
(74) *Attorney, Agent, or Firm*—Pennie & Edmonds LLP

(57) ABSTRACT

The present invention relates to a novel form of cross-linked high amylose starch and processes for its manufacture. Such cross-linked high amylose starch is useful as an excipient in a controlled-release pharmaceutical formulation when compressed with pharmaceutical agent(s) in a tablet. Such cross-linked high amylose starch is prepared by (a) cross-linking and chemical modification of high amylose starch, (b) gelatinization, and (c) drying to obtain a powder of said controlled release excipient. In a preferred embodiment, such cross-linked high amylose starch is prepared in the following steps: (1) granular cross-linking and additional chemical modification (e.g., hydroxypropylation) of high-amylose starch; (2) thermal gelatinization of the starch from step (1); and (3) drying the starch from step (2) to yield a powder capable of being used as a controlled release excipient.

43 Claims, 23 Drawing Sheets

U.S. PATENT DOCUMENTS

| | | | |
|---|---|---|---|
| 3,087,860 A | | 4/1963 | Endicott |
| 3,453,368 A | | 7/1969 | Magid |
| 3,490,742 A | | 1/1970 | Nichols et al. |
| 3,622,677 A | | 11/1971 | Short et al. |
| 4,026,986 A | | 5/1977 | Christen et al. |
| 4,072,535 A | | 2/1978 | Short et al. |
| 4,308,251 A | | 12/1981 | Dunn et al. |
| 4,369,308 A | | 1/1983 | Trubiano |
| 4,551,177 A | | 11/1985 | Trubiano et al. |
| 4,818,542 A | | 4/1989 | DeLuca et al. |
| 4,888,178 A | | 12/1989 | Rotini et al. |
| 4,904,476 A | | 2/1990 | Mehta et al. |
| 5,108,758 A | | 4/1992 | Allwood et al. |
| 5,456,921 A | | 10/1995 | Mateescu et al. |
| 5,807,575 A | * | 9/1998 | Dumoulin et al. .......... 424/464 |
| 5,830,884 A | | 11/1998 | Kasica et al. |
| 5,879,707 A | | 3/1999 | Cartillier et al. |

OTHER PUBLICATIONS

Lenaerts, et al., "Controlled release of theophylline from cross–linked amylose tablets", *Journal of Controlled Release* 15 (1991) 39–46.

Mateescu, "The use of cross linked amylose for the quantitative determination of alpha amylase and beta amylase in an amylolytic preparation", *Biochemie* 60 (1978) 535–537.

Nakano et al., "Preparation and Evaluation of Sustained Release Tablets Prepared with α–Starch", *Chem. Pharm. Bull.* 35(10) (1987) 4346–4350.

Salomon, et al., "Formulation des comprimés à libération prolongée I. Matrices inertes", *Pharm. Acta Helv.* 55 (1980) 174–182.

van Aerde, et al., "In vitro evaluation of modified starches as matrices for sustained release dosage forms", *Int. J. of Pharm.* 45 (1988) 145–152.

Visavagrungroj, et al., "Crosslinked Starch As Sustained Release Agent", *Drug Development and Industrial Pharmacy* 16(7) (1990) 1091–1108.

\* cited by examiner

CROSS-LINKED HIGH AMYLOSE STARCH FOR USE IN CONTROLLED-RELEASE PHARMACEUTICAL FORMULATIONS AND PROCESSES FOR ITS MANUFACTURE

FIELD OF INVENTION

The present invention relates to a novel form of cross-linked high amylose starch and processes for its manufacture. Such cross-linked high amylose starch is useful as an excipient in a controlled-release pharmaceutical formulation when compressed with a pharmaceutical agent(s) in a tablet.

BACKGROUND OF THE INVENTION

One of the critical factors influencing the rate of absorption of a drug administered as a tablet or other solid dosage form is the rate of dissolution of the dosage form in the body fluids of human or animal.

This factor is the basis for the so-called controlled-release, extended-release, sustained-release or prolonged-action pharmaceutical preparations that are designed to produce slow, uniform release and absorption of the drug over a period of hours, days, week, months, or years. Advantages of controlled-release formulations are a reduction in frequency of administration of the drug as compared with conventional dosage forms (often resulting in improved patient compliance), maintenance of a therapeutic effect over a set period of time, and decreased incidence and/or intensity of undesired side effects of the drug by elimination of the peaks in plasma concentration that often occur after administration of immediate-release dosage forms.

Many systems have been proposed and developed as matrices for the release of drugs. For example, polymeric materials such as polyvinyl chloride, polyethylene amides, ethyl cellulose, silicone and poly (hydroxymethyl methacrylate), have been proposed as vehicles for the slow release of drugs. See U.S. Pat. No. 3,087,860 to Endicott et al; U.S. Pat. No. 2,987,445 to Levesque et al.; Salomon et al., Pharm. Acta Helv., 55, 174–182 (1980); Korsmeyer, Diffusion Controlled Systems: Hydrogels, Chap. 2, pp 15–37 in Polymers for Controlled Drug Delivery, Ed. Tarcha, CRC Press, Boca Raton, Fla. USA (1991); Buri et al, Pharm. Acta Helv. 55, 189–197 (1980).

A substantial need exists for a controlled release composition that can deliver a variety of drugs, both hydrophilic and hydrophobic, in a consistent and reliable manner. Further, this composition should be amenable to all facets of tableting requirements, including, but not limited to, direct compression, appropriate hardness and resistance to friability, and compatibility with the active ingredient(s) contained in the tablet. Also, the composition should be easy to synthesize, biodegradable and non-toxic upon release of the drug.

One of the most widely studied compounds for controlled-release use has been starch, partially because it is biodegradable and is naturally metabolized by the human body [Kost et al., Biomaterials 11, 695–698 (1990)]. Starch has many uses in pharmaceutical products. It can act as a diluent, filler, carrier, binder, disintegrant, coating, thickener, and moisture sink. See U.S. Pat. No. 2,938,901 to Kerr et al., which discloses the use of granular starch cross-linked with sodium trimetaphosphate as a surgical dusting powder; U.S. Pat. No. 3,034,911 to McKee et al., which discloses the use of a cold water swelling and cold water insoluble starch in intact granular form as a disintegrant; U.S. Pat. No. 3,453,368 to Magid, which discloses the use of pregelatinized starches, optionally modified as binders for compressed ascorbic acid tablets; U.S. Pat. No. 3,490,742 to Nichols et al., which discloses a non-granular amylose (at least 50%) obtained from the fractionation of corn starch for use as a binder disintegrant in direct compression and dry granulation tablets; U.S. Pat. No. 3,622,677 to Short et al., which discloses the use of a partially cold water soluble and cold-water swelling starch, derived from a compacted granular starch, as a binder-disintegrant; U.S. Pat. No. 4,072,535 to Short et al., which discloses a pre-compacted starch having birefringent granules, non-birefringent granules, and some aggregates and fragments for use as a binder-disintegrant; U.S. Pat. No. 4,026,986 to Christen et al., which discloses the use of water-soluble starch ethers (e.g., hydroxyalkyl ethers) containing at least 50% amylose for use in forming capsule shells; U.S. Pat. No. 4,308,251 to Dunn et al., which discloses the use of corn, rice, potato and modified starches as an erosion-promotion agent in controlled release formulations prepared by wet granulation; U.S. Pat. No. 4,551,177 to Trabiano et al., which discloses the use of acid- and/or alpha-amylase converted starches as tablet binders; U.S. Pat. No. 4,904,476 to Mehta et al., which discloses the use of sodium starch glycolate as a disintegrant; U.S. Pat. No. 4,818,542 to DeLuca et al., which discloses starch as a biodegradable or bioerodible polymer for porous microspheres possibly coated with a cross-linking agent to inhibit or control drug release; U.S. Pat. No. 4,888,178 to Rotini et al., which discloses the use of starch, preferably maize starch, and sodium starch glycolate as disintegrants in the immediate release of a programmed release Naproxen® formulation containing immediate release and controlled release granulates in the form of tablets, capsules, or suspension in a suitable liquid media; U.S. Pat. No. 5,004,614 to Staniforth, et al., which discloses the use of starches as pharmaceutical fillers in controlled release devices containing an active agent and a release agent and the use of cross-linked or un-cross-linked sodium carboxymethyl starch for the coating.

U.S. Pat. No. 4,369,308 to Trubiano et al. discloses modified starches which are low swelling in cold water and which are suitable for use as disintegrants in compressed tablets. This is achieved by cross-linking and pregelatinizing in the presence of water, a cold-water insoluble, granular starch, drying the cross-linked, pregelatinized starch if necessary, and then pulverizing the dry starch. No controlled release properties are disclosed or claimed for these starches.

Cross-linked starch has been previously evaluated as a sustained release agent. Visavarungroj et al. [Drug Development And Industrial Pharmacy, 16(7), 1091–1108 (1990)] discloses the evaluation of different types of cross-linked starches and pregelatinized cross-linked starches for their use as hydrophilic matrices. It was determined that cross-linked starches demonstrated a poor swelling power and dispersion viscosity in comparison to pre-gelatinized starch and pregelatinized cross-linked starch. The study concluded that cross-linked modified waxy corn starches, either pregelatinized or not, in comparison to purely pregelatinized waxy corn starch are not suitable to use as a hydrophilic matrix in sustained release formulation.

Nakano et al. [Chem. Pharm. Bull. 35(10), 4346–4350, (1987)] disclose the use of physically modified starch (pregelatinized starch) as an excipient in sustained-release tablets. This article does not mention the specific role of amylose present in starch nor does it even mention amylose.

Van Aerde et al. [Int. J. Pharm., 45, 145–152, (1988)] disclose the use of modified starches obtained by drum-drying or extrusion pregelatinization, particle hydrolysis or cross-linking with sodium trimetaphosphate, as an excipient in sustained-release tablets. Once again, the article does not mention the specific role of amylose present in starch nor does it even mention amylose.

Herman et al. [Int. J. Pharm., 56, 51–63 & 65–70, (1989) and Int. J. Pharm., 63 201–205, (1990)] disclose the use of thermally modified starches as hydrophilic matrices for controlled oral delivery. This article discloses that thermally modified starches containing a low amount of amylose (25% and lower) give good sustained release properties, contrary to high amylose content starches which present bad controlled release properties.

U.S. Pat. No. 3,490,742 to Nichols et al. discloses a binder-disintegrant comprising non-granular amylose. This material is prepared either by fractionating starch or by dissolving granular high amylose starch in water at an elevated temperature. No controlled release properties are disclosed.

U.S. Pat. No. 5,108,758 to Alwood et al. discloses an oral delayed release composition comprising an active compound and glassy amylose. The composition is particularly adapted for achieving selective release of the active compound into the colon. The delayed release is due to a coating. Glassy amylose is one of the two forms of predominantly amorphous amylose, the other being a rubbery form. Here, the glassy amylose delays the release of the active compound from the composition in an aqueous environment but allows its release on exposure to an enzyme capable of cleaving the amylose. The amylose used in this composition is isolated from smooth-seeded pea starch and purified by precipitation from aqueous solution as a complex with n-butanol. The alcohol is then removed from an aqueous dispension of that complex by blowing through a suitable heated inert gas. As aforesaid, the release mechanism is based on an enzymatic reaction. There is no continuous release through the gastrointestinal tractus, but only a delayed release due to the degradation of the coating into the colon. Moreover, it is disclosed that the glassy amylose should preferably not contain hydroxy groups in a derivative form.

European patent application No. EP-A-499,648 to Wai-Chiu et al. discloses a tablet excipient. More particularly, they disclose a starch binder and/or filler useful in manufacturing tablets, pellets, capsules or granules. The tablet excipient is prepared by enzymatically debranching starch with an α-1,6 D-glucanohydrolase to yield at least 20% by weight of "short chain amylose." No controlled release properties are claimed for this excipient. Moreover, starch (unmodified, modified or cross-linked) must be enzymatically treated with an α-1,6-D-glucanohydrolase to be debranched and to yield the so-called "short chain amylose". Thus, starch with a high content of amylopectin is obviously preferred and amylose is rejected as not suitable because it is impossible to debranch amylose, since amylose has no branching. The role of amylose is not only ignored but considered negatively.

Mateescu et al. [U.S. Pat. No. 5,456,921] and Lenaerts et al. [J. Controlled Rel. 15, 39–46, (1991)] disclose that cross-linked amylose is a very efficient tool for controlled drug release. Cross-linked amylose is produced by reaction of amylose with a cross-linking agent such as epichlorohydrin, in an alkaline medium. Different degrees of cross-linking can be obtained by varying the ratio of epichlorohydrin to amylose in the reaction vessel. Tablets prepared by direct compression of a dry mixture of cross-linked amylose and a drug swell in solution and show a sustained release of the drug. Depending on the degree of cross-linking of the matrix, different degrees of swelling are obtained. Increasing the degree of cross-linking of amylose first generates an increase of drug-release time, followed by a decrease of drug-release time. The peak drug-release time is observed at a cross-linking degree value of 7.5. A further increase in the degree of cross-linking leads to an accelerated drug release from the cross-linked amylose tablets as a consequence of the erosion process. For cross-linking degree equal or greater than 7.5, increasing the degree of cross-linking of amylose generates a decrease of drug-release time. With degrees of cross-linking above 11, the swollen polymeric matrix presents in vitro disintegration over a period of approximately 90 minutes.

Mateescu et al. [International laid-open patent application No. WO 94/02121] and Dumoulin et al. [Intern. Symp. Control. Rel. Bioact. Mater. 20, 306–307, (1993)] disclose an enzymatically-controlled drug release system based on the addition of α-amylase within the cross-linked amylose tablet. α-amylase is able to hydrolyse α-1,4-glucosidic bonds present in the cross-linked amylose semi-synthetic matrix. Increasing the amount of α-amylase (5 to 25 EU) within the tablets induces a significant decrease in release time from 24 to 6 hours. Hence, drug release is controlled by two sequential mechanisms: (a) hydration and swelling of cross-linked amylose tablets followed by (b) internal enzymatic hydrolysis of the hydrated gel phase.

Cartilier et al. [International laid-open patent application WO 94/21236] disclose powders of cross-linked amylose having a specific cross-linking degree for use as a tablet binder and/or disintegrant. The tablets are prepared by direct compression. The concentration of cross-linked amylose in the tablets is lower than 35% by weight. Degrees of cross-linking from 6 to 30 and more particularly from 15 to 30 are preferred when disintegration properties are required.

U.S. Pat. No. 5,830,884 to Kasica et al. discloses thermally inhibited starches which are used in pharmaceutical products as a diluent, filler, carrier, binder, disintegrant, thickening agent, and coating. They are prepared by dehydrating the starch to a substantially anhydrous or anhydrous state and heat treating the anhydrous or substantially anhydrous starch for a period of time and at a temperature sufficient to inhibit the starch. Starches that are substantially thermally inhibited resist gelatinization and only mimic chemically cross-linked starch.

U.S. Pat. No. 5,879,707 to Cartilier et al. relates to the use of substituted amylose as a matrix for sustained drug release. The sustained release matrix is made of substituted amylose, prepared by reacting in an alkaline medium, amylose, with an organic substituent having a reactive functionality that reacts with the hydroxy groups of the amylose molecule. This substituent is preferably an epoxy or halogen alkane or alcohol. However, only linearly substituted amylose is used and is distinguished from cross-linked amylose which is used in the present invention.

Dumoulin et al. [International laid-open patent application No. WO 98/35992] disclose a process for the manufacture of a slow release excipient consisting mainly of cross-linked amylose having controlled-release properties, for use in the preparation of tablets or pellets. A starch containing a high amount of amylose (high amylose starch) is first subjected to gelatinization. The gelatinized high amylose starch is cross-linked with 1–5 grams of a cross-linking agent per 100 g of dry-based gelatinized high amylose starch in an alkali medium, creating a reaction medium containing a reaction product consisting of a cross-linked high amylose starch slurry. The obtained reaction medium is then neutralized, thereby forming by-products consisting of salts, which are removed from the reaction medium. The recovered cross-linked high amylose starch slurry is then subjected to a thermal treatment at a temperature of at least 60° C. and the thermally treated product is dried to obtain the slow-release excipient which contains a substantial amount of impurities.

Lenaerts et al. [J. Controlled Release 53, 225–234 (1998)] have demonstrated that gelatinized cross-linked high amylose starches are useful excipients for the formulation of controlled-release solid dosage forms for the oral delivery of drugs. These excipients exhibit a lack of erosion, limited swelling and the fact that increasing cross-linking degrees results in increase water uptake, drug release rate and equilibrium swelling. These investigators were also able to demonstrate that cross-linked high amylose starch matrices have the lowest inter-subject variability amongst the systems tested and demonstrate a total absence of food effect. Lenaerts et al. were also able to conclude that as the degree of cross-linking increased, the drug would be released faster. The authors concluded that for the gelatinized cross-linked high amylose starch to possess the characteristics needed to have a controlled release of the incorporated drugs, it is necessary that the surface of amylopectin clusters be coated by amylose chemically bound to amylopectin by the cross-linking procedure. This structure is indeed the one obtained by first gelatinizing the high amylose starch to extract amylose from the granules and then carrying out the chemical reaction to chemically bind amylose to the surface of amylopectin clusters, such as when using the process described by Dumoulin et al. in WO 98/35992.

All of the above references which relate to cross-linked high amylose starch teach that the starting amylose material be gelatinized prior to cross-linking. The integrity of starch granules in the dry state is dependent upon the hydrogen bonding between amylopectin and amylose. When an aqueous suspension of starch is heated to a certain temperature, the hydrogen bonding between amylopectin and amylose weakens and the granule swells until collapsing. This process is referred to as "gelatinization." This first step of the process permits leaching of the amylose from the starch granules prior to reaction with a cross-linking reagent, which then creates a cross-linked amylose with controlled-release properties. Moreover, it has been stated that gelatinization of high-amylose starch before cross-linking is required in order to prepare a product possessing the desired controlled-release property. See Dumoulin et al., WO 98/35992.

SUMMARY OF THE INVENTION

It has now been surprisingly found that high amylose starch can be subjected to chemical treatment (i.e., cross-linking and hydroxypropylation) in the granular state using very low concentrations of chemical reagent, followed by gelatinization and drying to yield a controlled-release excipient superior in release properties to high-amylose starch excipients produced by a process in which the high amylose starch is subjected to gelatinization as a first step, followed by chemical treatment and drying.

The novel processes, compositions and controlled release activity described herein is counterintuitive to what has been generally known to those skilled in the art. By exposing high amylose starch to chemical treatment (i.e., cross-linking) prior to gelatinization, one skilled in the art would not expect the production of a product exhibiting controlled-release characteristics. Cross-linking of high-amylose starch prior to gelatinization would likely lead to material that would not exhibit controlled release properties, but would resemble an immediate release profile as the cross-linked high amylose starch would be unable to support a matrix capable of controlled release thereby demonstrating essential structural differences between the two cross-linked products. According to Lenaerts et al. (J. Controlled Rel., 1998) such structural differences would lead to an incapacity of the material to have controlled release properties. Jane et al. [Cereal Chemistry, 69(4), 405–409 (1992)] disclose that cross-linking of pregelatinized and dispersed starch causes less difference in the proportion of soluble amylose and amylopectin than did the cross-linking of native granular starch. Jane et al. report no increase in the size of amylose as a result of cross-linking between two or more amylose molecules after the starch had been cross-linked in the granular form and do not mention any controlled release property of the starches cross-linked in the granular form. In addition, Mateescu et al. (U.S. Pat. No. 5,456,921) describe that optimal controlled release is obtained at an amount of cross-linking agent of 7.5 g per 100 g dry starch whereas in the present invention the cross-linking reagent can be added at an amount lower than 0.3 g per 100 g dry starch. This low amount of cross-linking reagent is preferred because it also allows the product to be covered by the monographs for modified food starch of the US Food and Drug Administration and the Food Chemicals Codex as well as the European Parliament and Council Directive Nr/95/2/EC of Feb. 20, 1995 on Food additives other than Colours and Sweeteners (Miscellaneous Directive).

Remarkably, it has been discovered that a novel controlled-released excipient may be prepared in following steps:

(1) granular cross-linking and additionally chemical modification (e.g., hydroxypropylation) of high-amylose starch;

(2) Thermal gelatinization of the starch from step (1); and (3) Drying the starch from step (2) to yield a powder capable of being used as a controlled release excipient.

The advantages of this excipient include, but are not limited to: (1) ease in processing, (2) avoidance of any organic solvents in the process, (3) ability to obtain high purity products meeting FDA regulations and the Food Chemical Codex as well as the European Parliament and Council Directive Nr 95/2/EC of Feb. 20, 1995 on Food additives other than Colours and Sweeteners (Miscellaneous Directive), (4) the ability to make direct compression tablets, (5) compatibility with hydrophilic and hydrophobic drugs, (6) compatibility with a large range of drug concentrations and solubilities, (7) the safety of cross-linked high amylose starch, (8) an excellent robustness vis-à-vis production and dissolution parameters, (9) an excellent batch-to-batch reproducibility, and (10) a simple and predictable scale-up.

Most particularly, it has been discovered that the controlled release of a drug can be achieved with high-amylose starch that undergoes the sequential transformation described above to produce a powder excipient. Use of this modified starch as a matrix in a tablet produces a remarkable, almost linear release profile and a release time of 2 hours to 24 hours.

It has also been found that this modified starch can be used for the production of implants for local sustained delivery of drugs with an in vivo release extending to periods of 1 to 3 days to 3 to 4 weeks.

In accordance with the invention, there is provided a pharmaceutical formulation comprising a controlled release tablet, further comprising a direct compression blend of a powder of cross-linked and additionally modified high amylose starch as the controlled-release excipient for the drug and powder of at least one drug. The controlled release matrix consists essentially of cross-linked high amylose starch obtained by cross-linking high amylose starch with a suitable cross-linking agent. Additionally, the cross-linked high amylose starch is chemically modified. The sequence of the two reactions (i.e., cross-linking reaction and additional chemical modification) may be performed alternatively in the reverse order or at the same time.

The cross-linked high amylose starch may be obtained with a preferred range of amount of cross-linker between about 0.005 to 0.3 g per 100 g dry starch.

When the pharmaceutical drug(s) used in this invention are very slightly soluble in water, the powder of such drug(s) may represent up to about 70% to about 90% of the weight of the tablet. If the pharmaceutical drug(s) used is highly soluble, it should not exceed about 30% to about 50% of the weight of the tablet.

The tablet according to the invention can also be of the dry coated type. In this case, the core of the tablet contains most of the powder of said drug(s). The outside shell will consist primarily of the controlled release excipient except if special delivery profiles (e.g. Biphasic or double pulse) are necessary.

Thus, the invention as broadly defined provides a process for the manufacture of a novel controlled release excipient consisting mainly of cross-linked high amylose starch for use in the preparation of tablets. Such process comprises:

(a) cross-linking high amylose starch (preferably such high amylose starch contain at least 70% w/w of amylose), preferably with about 0.005 g to about 0.3 g, more preferably about 0.01 g to about 0.12 g, even more preferably about 0.04g to about 0.1 g, most preferably about 0.075 g, cross-linking reagent per 100 g of dry-based high amylose starch in an alkaline aqueous medium at a suitable temperature (preferably about 10° C. to about 90° C., more preferably about 20° C. to about 80° C., even more preferably 20° C. to about 60° C., and most preferably about 30° C.), for a suitable reaction time period preferably about 1 minute to about 24 hours, more preferably of about 15 minutes to about 4 hours, even more preferably of about 30 minutes to about 2 hours, and most preferably of about 60 minutes), thereby forming a reaction medium containing a reaction product consisting of a cross-linked high amylose starch slurry (preferably of a concentration of about 5% to about 45%, more preferably of about 20% to about 42%; even more preferably of about 30% to about 40%, and most preferably of about 35%).

(b) subjecting the cross-linked high amylose starch slurry from step (a) to chemical modification (e.g., hydroxypropylation with propylene oxide, preferably about 0.5% to 20%, more preferably about 1 to about 10%, even more preferably of about 3 to 9%, and most preferably of about 6% propylene oxide), at a temperature of about 10° C. to about 90° C., preferably of about 20° C. to about 80° C., more preferably of about 20° C. to about 50° C., and most preferably of about 40° C., for a time period of about 1 hour to about 72 hours, preferably of about 2 hours to about 48 hours, more preferably of about 10 hours to about 40 hours, and most preferably for about 29 hours;

Alternatively, steps (a) and (b) are performed in the reverse order or at the same time (c) neutralizing the reaction medium obtained in step (b) with an acid (preferably a dilute aqueous inorganic acid), washing the slurry formed and optionally dewatering or drying;

(d) forming a slurry at a concentration of about 2% w/w to about 40% w/w, preferably of about 5% w/w to about 35% w/w, more preferably of about 5% w/w to about 25% w/w, and most preferably of about 9% w/w, adjusting the pH to a desired value between 3 and 12 (preferably about 6.0), and gelatinizing the slurry at a temperature of about 80° C. to about 180° C., preferably of about 120° C. to about 170° C., more preferably of about 140° C. to about 165° C., and most preferably of about 160° C., for about 1 second to about 120 minutes, preferably of about 30 seconds to about 60 minutes, more preferably of about 1 minute to about 20 minutes, and most preferably of about 8 minutes; and (e) drying the thermally treated product obtained in step (d) to obtain the controlled release excipient consisting mainly of chemically modified and cross-linked high amylose starch in the form of a powder.

DETAILED DESCRIPTION OF THE INVENTION

Figure 1:
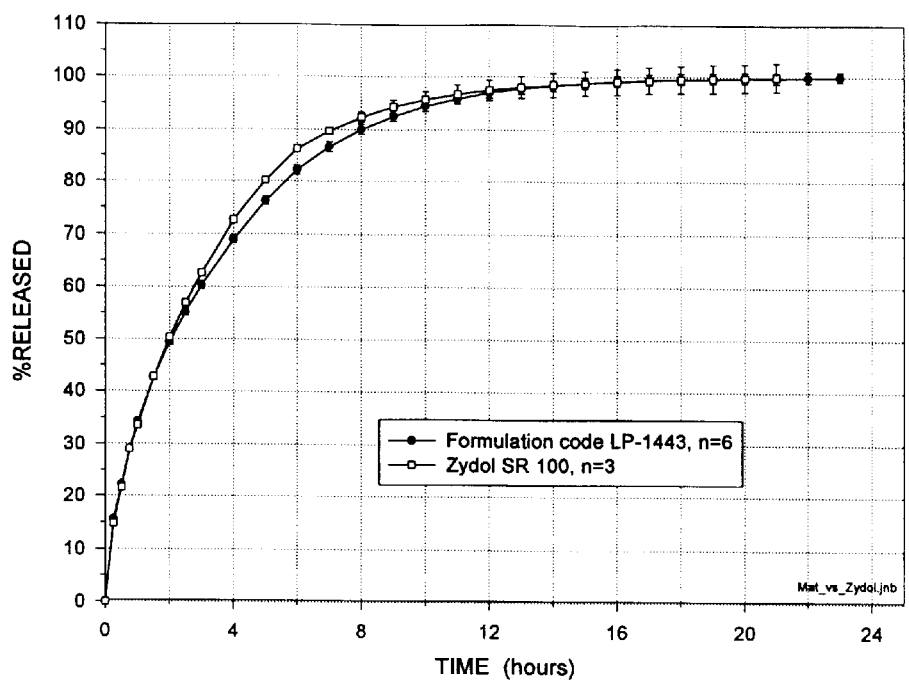
FIG. 1: Release profiles under standard dissolution conditions for formulation LP-1443 and Zydol SR 100®.

Starch is one of the most ubiquitous biopolymers on earth. Starch is mainly a carbohydrate which is composed of two distinct fractions: amylose which is essentially a linear polymer of glucopyranose units linked through $\alpha$-D-(1,4) linkages. The second component is amylopectin which is a highly branched polymer which is linked to the C-6 hydroxyl position of certain glucose moieties in amylose, via $\alpha$-D-(1,6) linkages. Amylose contains about 4,000 glucose units. Amylopectin contains about 100,000 glucose units.

Cross-linking of starch represents a powerful method for modifying starch. Usually, starch granules are cross-linked to increase resistance of the paste to shear or heat. Such chemically cross-linked starches provide a desirable smooth texture and possess viscosity stability throughout processing operations and normal shelf life. As mentioned, in accordance with the invention, it has been discovered that the cross-linking of high amylose starch followed by gelatinization is highly desirable. More specifically, it has been found that cross-linking high amylose starch with additional chemical modification (e.g., hydroxypropylation) prior to gelatinization produces a novel excipient possessing the desired controlled release properties.

The cross-linking of high amylose starch may be realized according to procedures described in the art. For example, cross-linking of amylose can be carried out in the manner described in Mateescu [BIOCHEMIE, 60, 535–537 (1978)] by reacting amylose with epichlorohydrin in an alkaline medium. In the same manner, starch can also be cross-linked with a reagent selected from the group consisting of epichlorohydrin, adipic acid anhydride, sodium trimetaphosphate and phosphorous oxychloride or other cross-linking agents including, but not limited to, 2,3-dibromopropanol, linear mixed anhydrides of acetic and di- or tribasic carboxylic acids, vinyl sulfone, diepoxides, cyanuric chloride, hexahydro-1,3,5-trisacryloyl-s-triazine, hexamethylene diisocyanate, toluene 2,4-diisocyanate, N,N-methylenebisacrylamide, N,N'-bis (hydroxymethyl) ethyleneurea, mixed carbonic-carboxylic acid anhydrides, imidazolides of carbonic and polybasic carboxylic acids, imidazolium salts of polybasic carboxylic acids, and guanidine derivatives of polycarboxylic acids.

The reaction conditions employed will vary with the type and amount of the cross-linking agent that is used, as well as the base concentration, amount and type of starch.

All available starches containing more than 40% w/w amylose can be used, e.g., pea and wrinkled pea starch, bean starch, hybrids or genetically modified tapioca or potato starch, or any other root, tuber or cereal starch. Preferably, high amylose starch containing about 70% w/w amylose is used as the base material. In the current examples 1 and 2, high amylose starch, CIAmyloGel 03003 (Cerestar U.S.A. Inc.) is applied. The reaction is usually performed in the presence of a sodium salt such as sodium sulfate or sodium chloride and a sodium base. These reagents are dispersed in water to a slurry of about 35% to about 42% dry substances. The slurry is then heated or cooled to temperature of about 10° C. to about 90° C., preferably about 20° C. to about 80° C., more preferably 20° C. to about 40° C., and most preferably about 30° C. For the present invention, it is preferred to use for the cross-linking step about 0.005% to about 0.3% w/w of cross-linking reagent, phosphorous oxychloride in an amount of between 0.01 and 0.2% (w/w) or sodium trimetaphosphate (STMP) in an amount of between 0.05 and 0.3% (w/w). In example 1 an amount of 0.075% phosphorous oxychloride is used and in example 2 an amount of 0.15% of sodium trimetaphosphate is used.

The cross-linking reaction is performed in an aqueous alkaline medium, of a pH of 10 to 14 for about 0.2 to 40 hours (preferably of about 15 minutes to about 4 hours, more preferably of about 30 minutes to about 2 hours, and most preferably of about 60 minutes) at a temperature of about 15 to about 90° C. A reaction mixture containing a cross-linked high amylose starch slurry is formed. The slurry concentration is preferably about 5% to about 45%, more preferably of about 20% to about 42%, and most preferably of about 30% to about 40%.

The cross-linked high amylose starch is additionally chemically modified. A preferred modification is hydroxypropylation with propylene oxide in a concentration of about 0.5% to about 20%, preferably about 1 to about 10% on d.b. The reaction mixture is kept at a temperature of about 10° C. to about 90° C., preferably of about 20° C. to about 80° C., more preferably of about 20° C. to about 50° C., and most preferably of about 40° C., for a time period of about 1 hour to about 72 hours, preferably of about 2 hours to about 48 hours, more preferably of about 10 hours to about 40 hours, and most preferably for about 20 hours. Alternatively the cross-linking and chemical modification can be performed in the reverse order or at the same time. The reaction mixture is neutralized with a dilute aqueous acid. Sulfuric acid and hydrochloric acid are the preferred acids for neutralization.

The cross-linking reaction carried out in an alkaline medium followed by neutralization leads to the formation of by-products mainly consisting of salts. Numerous methods can be used to remove salts from the aqueous slurry of cross-linked high amylose starch, including filtration, centrifugation, decantation, or continuous Dorr Clones washing.

In accordance with the present invention, any of these known methods could be used. The obtained starch slurry or cake can optionally be dewatered or dried to obtain a starch cake or a dry powder.

Starch granules are held together by the hydrogen bonding that occurs between starch molecules. When an aqueous suspension of starch is heated to a certain temperature, this hydrogen bonding weakens and the granules swell until collapsing. This process is called gelatinization.

Numerous methods of gelatinization are known in the art. They include indirect or direct heating or steam injection of an aqueous dispersion of starch, by chemical treatment of such dispersions using strong alkali, or a combination of mechanical and heat treatment.

In accordance with the invention, gelatinization of the cross-linked high amylose starch is preferably realized by diluting the starch slurry, starch cake or powder in water in order to form a slurry at a concentration of about 2 to 40% w/w. The pH of the modified starch slurry is adjusted to a desired value to about 3 to about 12. In the present case a pH of about 6.0 is desired. The slurry is then heated to about 80° C. to about 180° C., preferably of about 120° C. to about 170° C., more preferably of about 140° C. to about 165° C., and most preferably of about 160° C., by direct steam injection. The preferred method of gelatinization is by continuous pressure cooking of the starch slurry. The slurry is then held at this temperature for a time period of about 1 second to about 120 minutes, preferably of about 30 seconds to about 60 minutes, more preferably of about 1 minute to about 20 minutes, and most preferably of about 2–10 minutes, at a temperature of about 80° C. to about 180° C., preferably of about 120° C. to about 170° C., more preferably of about 140° C. to about 165° C., and most preferably of about 160° C. This procedure can be performed in a continuous system including a holding column (see Example 1).

The gelatinized product can be dried by lyophilization, by spray drying techniques using a spray nozzle or atomization disc, or in a heated chamber. In accordance with the invention, the cross-linked high amylose starch is spray-dried by using a spray-drying tower equipped with a nozzle. The inlet temperature is fixed at about 60° C. to about 350° C., preferably of about 150° C. to about 300° C., more preferably of about 200° C. to about 270° C., and most preferably of about 245° C. The air outlet temperature is set at about 40° C. to about 210° C., preferably of about 60° C. to about 190° C., more preferably of about 80° C. to about 170° C., and most preferably of about 120° C. The obtained powder is a controlled release excipient with the below described powder properties:

| Properties | |
|---|---|
| Moisture Content | 2–15% |
| Bulk Density | 100–350 g/l |
| Packed Density | 150–600 g/l |
| pH | 4–7 |
| Particle Size Peak Value (Laser Particle Sizer-Sympatec) | 20–250 μm |

Applicants have found that the modified cross-linked high amylose starch of the present invention is useful as a carrier polymer for pharmaceutical agents that are administered orally, in view of the resistance of tablets to degradation by digestive amylase and enhanced dissolution properties. Such modified cross-linked high amylose starch confers desirable slow-release properties to orally administered tablets containing pharmaceutical agents.

Applicants further found that tablets implanted subcutaneoulsy or intramuscularly were very well tolerated and highly biocompatible. They were totally scavenged by macrophages over a 1 to 3 month period. Such tablets were also shown to allow the controlled release of drugs locally for periods ranging from about 1 to about 3 days to about 3 to about 4 weeks.

Accordingly, the invention provides a solid controlled-release pharmaceutical dosage unit in the form of a tablet. A tablet, as understood by one skilled in the art, can be administered by various routes, e.g., ingested orally, used in the oral cavity, or used for implantation, etc. A tablet can also be in a variety of forms, e.g., uncoated , dry coated, or film coated, etc. A comprehensive discussion of tablets can be found in references such as i The Theory and Practice of Industrial Pharmacyby Lachman et al., 3rd Ed. (Lea & Febiger, 1986). The solid controlled-release pharmaceutical dosage unit of the present invention comprises a blend of about 0.01% to about 80% by weight of a pharmaceutical agent, and of about 20% to about 99.99% by weight of the modified cross-linked high amylose starch described above. The pharmaceutical agent is preferably in the form of a dry powder.

Such pharmaceutical agent is any drug that can be orally administered. Preferably, the pharmaceutical agent is, but more limited to, pseudoephedrine hydrochloride, acetaminophen or diclofenac sodium, verapamil, glipizide, nifedipine, felodipine, betahistine, albuterol, acrivastine, omeprazole, misoprostol, tramadol, oxybutynin, trimebutine, ciprofloxacin, and salts thereof. In addition, the pharmaceutical agent can be an antifungal agent, such as ketoconazole, or an analgesic agent such as acetylsalicylic acid, acetaminophen, paracetamol, ibuprofen, ketoprofen, indomethacin, diflunisol, naproxen, ketorolac, diclofenac, tolmetin, sulindac, phenacetin, piroxicam, mefamanic acid, dextromethorphan, other non-steroidal anti-inflammatory drugs including salicylates, pharmaceutically acceptable salts thereof or mixtures thereof.

The solid controlled-release pharmaceutical dosage unit may further include a pharmaceutically acceptable carrier or vehicle. Such carriers or vehicles are known to those skilled in the art and are found, for example, in *Remington's Pharmaceutical Sciences*, 18th Ed. (1990). Examples of such carriers or vehicles include lactose, starch, dicalcium phosphate, calcium sulfate, kaolin, mannitol and powdered sugar. Additionally, when required, suitable binders, lubricants, disintegrating agents and coloring agents can be included. If desired, dyes, as well as sweetening or flavoring agents can be included.

Binders suitable for use in pharmaceutical compositions and dosage forms include, but are not limited to, corn starch, potato starch, or other starches, gelatin, natural and synthetic gums such as xantham gum, acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, polyethylene oxide and mixtures thereof.

Suitable forms of microcrystalline cellulose include, for example, the materials sold as AVICEL-PH-101, AVICEL-PH-103 AVICEL RC-581, and AVICEL-PH-105 (available from FMC Corporation, American Viscose Division, Avicel Sales, Marcus Hook, Pa., U.S.A.). An exemplary suitable binder is a mixture of microcrystalline cellulose and sodium carboxymethyl cellulose sold as AVICEL RC-581. Suitable anhydrous or low moisture excipients or additives include AVICEL-PH-103™, Starch 1500 LM and CIPharm DC 93000.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder/filler in pharmaceutical compositions of the present invention is typically present in about 50 to about 99 weight percent of the pharmaceutical composition.

Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel (AEROSIL 200, manufactured by W. R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), or mixtures thereof. A lubricant can optionally be added, typically in an amount of less than about 1 weight percent of the pharmaceutical composition.

Once the pharmaceutical agent and modified cross-linked high amylose starch are blended, generally by conventional means, including, but not limited to, powder blending, dry or wet granulation, the resulting blend is compressed to form a tablet. Preferably, the pressure used to compress the blend is equal to or exceeds 0.16 T/cm$^2$.

The present invention will be more readily understood by referring to the following test methods and examples which are given to illustrate the invention rather than limit its scope.

EXAMPLES

The following procedures were used as test methods to evaluate the properties of the products prepared in the examples.

Example 1

Preparation of Controlled Release Excipient
A. Preparation of Cross-linked High Amylose Starch High amylose starch (30.0 kg) containing about 70% w/w of amylose (CI AmyloGel 03003) is placed in a reactor. To this reactor is added water (55.0 l) containing sodium hydroxide (30.0 g) and sodium sulfate (2.40 kg). The resulting slurry is heated to a temperature of 30° C. Phosphorus oxychloride (22.5 g) is added to the reaction mixture which is reacted for one hour.

B. Preparation of Hydroxypropylated Cross-Linked High Amylose Starch

The crude reaction mixture from Part A is transferred into a hydroxypropylation reactor. The reaction mixture is heated to 40° C. over 30 minutes and the reaction is purged with nitrogen. After a full purge, propylene oxide (1.80 kg) is added. The reaction mixture is kept at 40° C. for 20 hours. The reaction mixture is neutralized with 0.1N H$_2$SO$_4$ (1:2 v/v) to a pH of 5.5. The starch slurry is washed with a basket-centrifuge at a speed of 1200 rpm. The obtained starch cake is re-slurrified in 35l of water and centrifuged a second time. The resulting starch cake is dried in a flash dryer at an inlet temperature of 160° C. and an outlet temperature of 60° C.

C. Gelatinization

The modified granular starch cake is diluted in demineralized water in order to form a slurry at a concentration of about 8% calculated on dry substance. The resulting slurry has a relative density of 1.032 kg/l compared to water. The pH of the modified starch slurry is adjusted to 6.0. The slurry is then heated to 160° C. by direct steam injection (Schlick Model 825). The temperature variation is not higher than ±1° C. The slurry is held in a holding column for a period of 4 minutes at a temperature of 160° C. and a pressure of about 5.5 bar. The pressure is then reduced to atmospheric by passing through a flash. The slurry is then contained at 95° C. in a hold tank.

D. Spray-Drying

The drying of the slurry from Part C is carried out using a Niro FSD 4 spray-drying tower equipped with a 0.8 mm nozzle and fed at 10 l/hour. The inlet temperature is fixed at 300° C. and the outlet temperature of 120° C. The obtained powder is a controlled release excipient with the following properties:

| Properties | |
| --- | --- |
| Moisture Content | 4.5% |
| Bulk Density | 150 g/l |
| Packed Density | 210 g/l |
| pH | 5.4 |
| Particle Size Peak Value (Laser Particle Sizer-Sympatec) | 50 μm |

The starch sample obtained through (A)–(D) is hereafter referred to as "Cerestar."

Example 2

Preparation of Controlled Release Excipient
A. Preparation of Cross-linked High Amylose Starch High amylose starch (30.0 kg) containing about 70% w/w of amylose (CI AmyloGel 03003) is placed in a reactor. To this reactor is added water (55.0l) containing sodium hydroxide (30.0 g) and sodium sulfate (2.40 kg). The resulting slurry is heated to a temperature of 30° C. Sodium trimetaphosphate (45 g) is added to the reaction mixture which is reacted for one hour.

B. Preparation of Hydroxypropylated Cross-Linked High Amylose Starch

The crude reaction mixture from Part A is transferred into a hydroxypropylation reactor. The reaction mixture is heated to 40° C. over 30 minutes and the reaction is purged with nitrogen. After a full purge, propylene oxide (1.80 kg) is added. The reaction mixture is kept at 40° C. for 20 hours. The reaction mixture is neutralized with 0.1N H$_2$SO$_4$ (1:2 v/v) to a pH of 5.5. The starch slurry is washed with a basket-centrifuge at a speed of 1200 rpm. The obtained starch cake is re-slurrified in 35l of water and centrifuged a second time. The resulting starch cake is dried in a flash dryer at an inlet temperature of 160° C. and an outlet temperature of 60° C.

C. Gelatinization

The modified granular starch cake is diluted in demineralized water in order to form a slurry at a concentration of about 8% calculated on dry substance. The resulting slurry has a relative density of 1.032 kg/l compared to water. The pH of the modified starch slurry is adjusted to 6.0. The slurry is the heated to 160° C. by direct steam injection (Schlick Model 825). The temperature variation is not higher than ±1° C. The slurry is held in a holding column for a period of 4 minutes at a temperature of 160° C. and a pressure of about 5.5 bar. The pressure is then reduced to atmospheric by passing through a flash. The slurry is then contained at 95° C. in a hold tank.

D. Spray-Drying

The slurry from Part C is carried out using a Niro FSD 4 spray-drying tower equipped with a 0.8 mm nozzle and fed at 10 l/hour. The inlet temperature is fixed at 300° C. and the outlet temperature of 120° C. The obtained powder is a controlled release excipient with the following properties:

| Properties | |
|---|---|
| Moisture Content | 5.2% |
| Bulk Density | 103 g/l |
| Packed Density | 155 g/l |
| pH | 5.3 |
| Particle Size Peak Value (Laser Particle Sizer-Sympatec) | 70 μm |

Example 3

Preparation of Controlled Released Tramadol HCl 100 mg Tablets

Tramadol HCl 100 mg tablets were prepared in a matrix dosage form (Formulation LP-1443) with cross-linked high amylose starch prepared as described in Example 1. The components of Formulation LP-1443 are listed in Table 1. The Formulation LP-1443 tablets have a diameter of 9.53 mm. The shape of an LP-1443 tablet is round and biconvex. For comparison, Tramal Long 100® (manufactured by Grünenthal, Germany) was used. Tramal Long 100® contains 100 mg of Tramadol HCl and are in a matrix dosage form with a diameter of 10.15 mm. The shape of Tramal Long 100® is round and biconvex.

TABLE 1

Description of formulation LP-1443

| Ingredients | Quantity per tablet (mg) | % (w/w) |
|---|---|---|
| Tramadol HCl | 100 | 30.77 |
| cross-linked high amylose starch | 188.6 | 59.03 |
| Xanthan gum | 32.5 | 9 |
| Talc (USP) | 3.25 | 1 |
| SiO$_2$ | 0.65 | 0.2 |
| TOTAL | 325 | 100 |

Example 4

Preparation of Controlled Released Tramadol HCl 200 mg Tablets without Immediate Release Film coating [LP-1473 without film coating]

Tramadol HCl 200 mg tablet without film coating were prepared according to Table 2. First, tramadol HCl powder, cross-linked high amylose starch, Talc, and SiO$_2$ were mixed and compressed to form the core of the tablet. Next, tramadol HCl, cross-linked high amylose starch, xantham gum, Talc and SiO$_2$ were mixed and compressed to form a dry-coating outside the tablet core. A biphasic tablet containing 170 mg tramadol HCl was formed. Such a tablet is referred to as LP-1473 without film coating.

TABLE 2

Description of formulation LP-1473 (200 mg TRAMADOL HCl) (without the 30 mg tramadol immediate release film coating)

| Ingredients | Quantity per tablet (mg) | % (w/w) |
|---|---|---|
| CORE | | |
| Tramadol HCl | 85 | 42.5 |
| cross-linked high amylose starch | 188.6 | 56.3 |
| Talc (USP) | 3.25 | 1 |
| SiO$_2$ | 0.65 | 0.2 |
| TOTAL | 200 | 100 |
| DRY COATING | | |
| Tramadol HCl | 85 | 21.25 |
| cross-linked high amylose starch | 230.2 | 57.55 |
| Xanthan gum | 80 | 20 |
| Talc (USP) | 4 | 1 |
| SiO$_2$ | 0.8 | 0.2 |
| TOTAL | 400 | 100 |

Example 5

Preparation of Film Coated Formulation LP-1473

Drycoated tablets of formulation code LP-1473 discussed in Example 4 were further coated with a film containing 30 mg of tramadol HCl. The film consists of a first coating containing 30 mg tramadol HCl mixed with 8 mg Opadry Clear® YS-3-7065. This subcoat was then covered with 13 mg of white Opadry II® Y-22-7719. Opadry Clear® and Opadry II® are manufactured by Colorcon, Inc., West Point, Pa.

Example 6

Determination of Tramadol HCl Concentration After Dissolution

Concentration of tramadol HCl released in dissolution vessels was assayed directly by UV-Visible spectrophotometry using a Spectrophotometer UV-Visible HP-8453. Collected fractions were analyzed by measuring UV absorption in the range 269 to 273 nm using a 1 nm displacement, against a reference signal measured in the range of 380 to 384 nm using a 1 nm displacement. Calibrations curves in U.S.P. standard buffer pH 1.2 and pH 7.5 were determined in the concentration range of 0.0300 mg/mL to 0.800 mg/mL. The curves at both pH values being identical, the curve determined at pH 1.2 was used for all assays.

Example 7

Testing Dissolution Under Standard Dissolution Conditions

All tests were conducted on a Vankel BioDiss (U.S.P. type III) dissolution test station. To conduct test under standard dissolution conditions, the BioDiss was configured with four rows of dissolution vessels. The vessels were filled each with 250.0 g of dissolution medium. The dissolution medium was either U.S.P. standard buffer pH 1.2, U.S.P. standard buffer pH 6.8 (50 mM), or U.S.P. standard buffer pH 7.5 (50 mM). The enzyme used was α-Amylase Bacillus from Sigma Chemicals. The cells containing the tablets were fitted with a 40 mesh screen in the lower caps and a 20 mesh screen in the upper caps. To mimic in vivo condition, dissolution tests were conducted at 37° C. for 24 hours as outlined below:

| TIME (hours) | pH | Enzyme (I.U./L) | Agitation dips/min |
|---|---|---|---|
| 00:30 | 1.2 | 0 | 15 |
| 00:30 | 6.8 | 4500 | 15 |
| 04:00 | 7.5 | 0 | 15 |
| 19:00 | 7.5 | 0 | 5 |

Each dissolution medium was sampled at specific time points. Each aliquot was filtered through a 2 mm filter (Millex AP) prior to assay using a UV-Visible spectrophotometer (see Example 6). The dissolution profiles under standard dissolution condition of LP-1443, Tramal Long 100® (also known as Zydol SR 100® in the United Kingdom), LP-1473 (without film coating) and LP-1473 (with film coating) were obtained.

FIG. 1 shows the release profile obtained for a 100 mg tramadol HCl formulation (formulation code LP-1443). The figure also contains the profile of the reference product, Zydol SR 100®. The data show that formulation LP-1443 and the references have comparable dissolution profiles.

Figure 2:
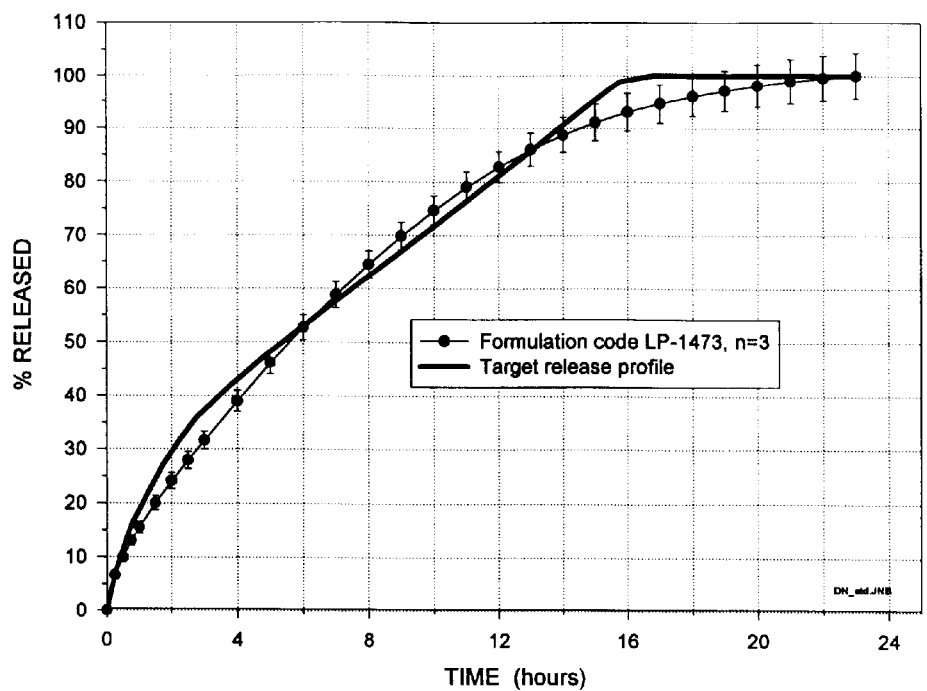
FIG. 2: Target and actual in-vitro dissolution profiles for formulation LP-1473. In-vitro profile was obtained under standard dissolution conditions.

FIG. 2 shows the target and actual release profiles obtained with formulation LP-1473 (without film coating) for the 170 mg tramadol HCl slow release component of the overall 200 mg formulation.

Figure 3:
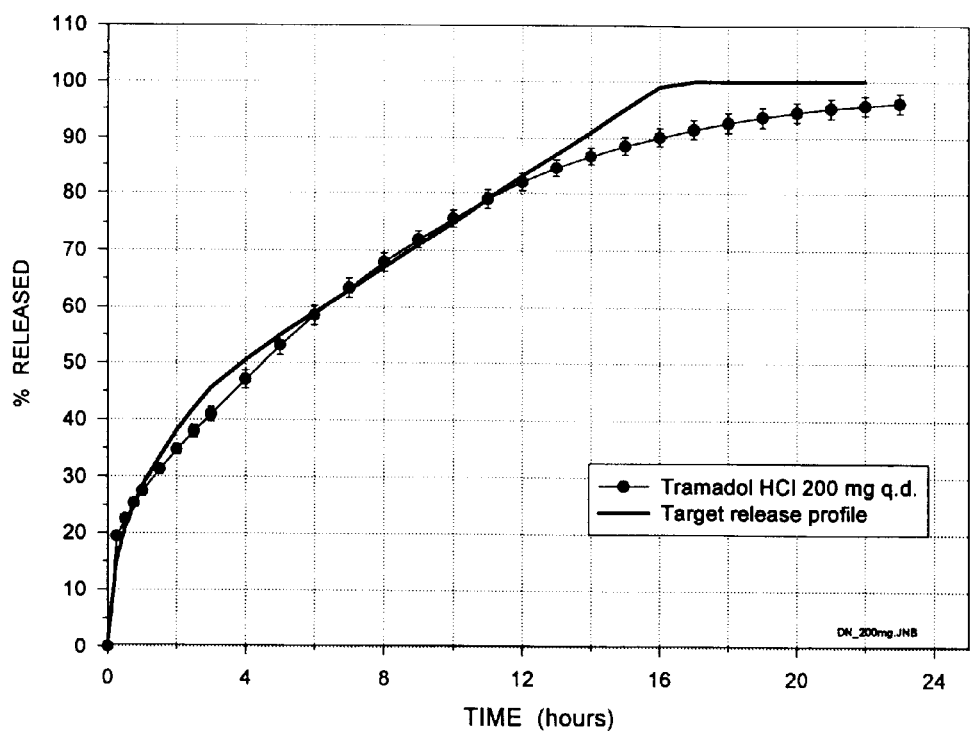
FIG. 3: Target and in-vitro dissolution profile for Tramadol® HCl 200 mg.

FIG. 3 contains the in-vitro dissolution profile of the film coated 200 mg tramadol HCl formulation, along with the target release profile for the overall 200 mg tramadol HCl tablet.

The target curves were computed from a target pharmacokinetic profile, the latter being defined by a quick onset of action (concentration in excess of 100 ng/mL in less than 1 hour), a 16 hour plateau in the 100 to 300 ng/mL range of concentrations and a slow decay with a concentration at 24 hour around 100 ng/mL.

Example 8

In Vivo Bioavailability

The bioavailability of Tramal Long 100®, LP-1443 tablets and LP-1473 (with film coating) tablets was assessed under in vivo conditions in an open-label, single-dose, randomized, cross-over pharmacokinetic study performed in 14 healthy human volunteers.

Figure 4:
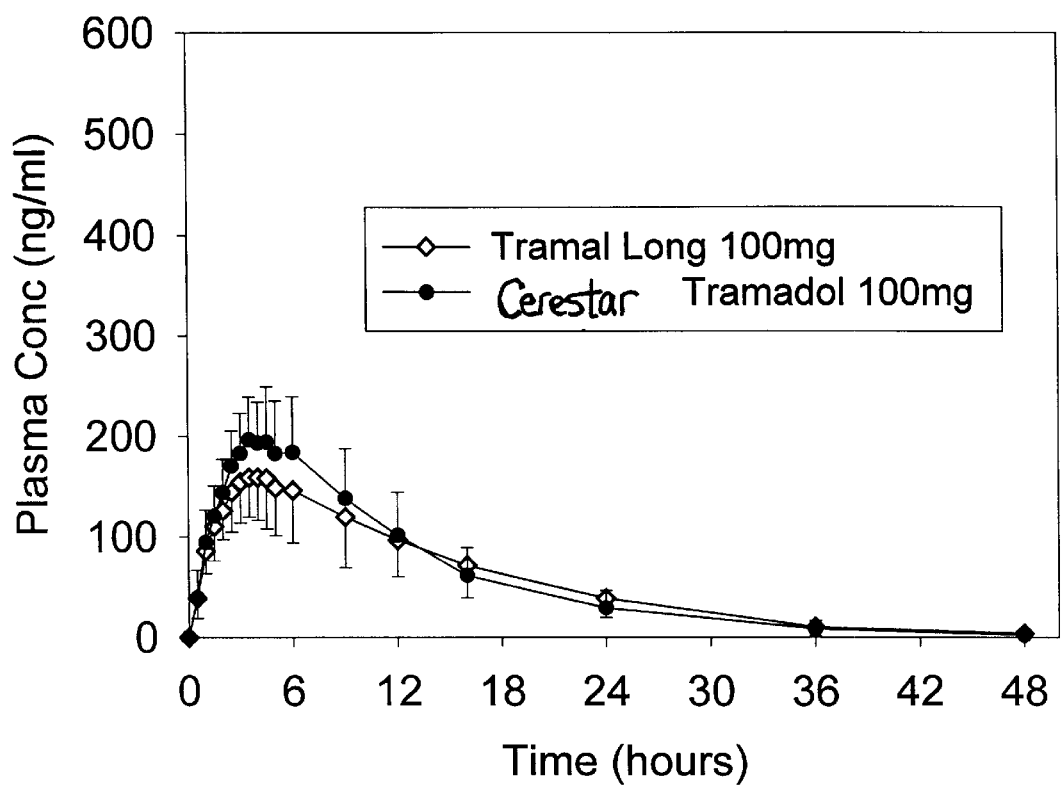
FIG. 4: Human pharmacokinetics of tablets LP-1443 versus Tramal Long 100®.
Figure 5:
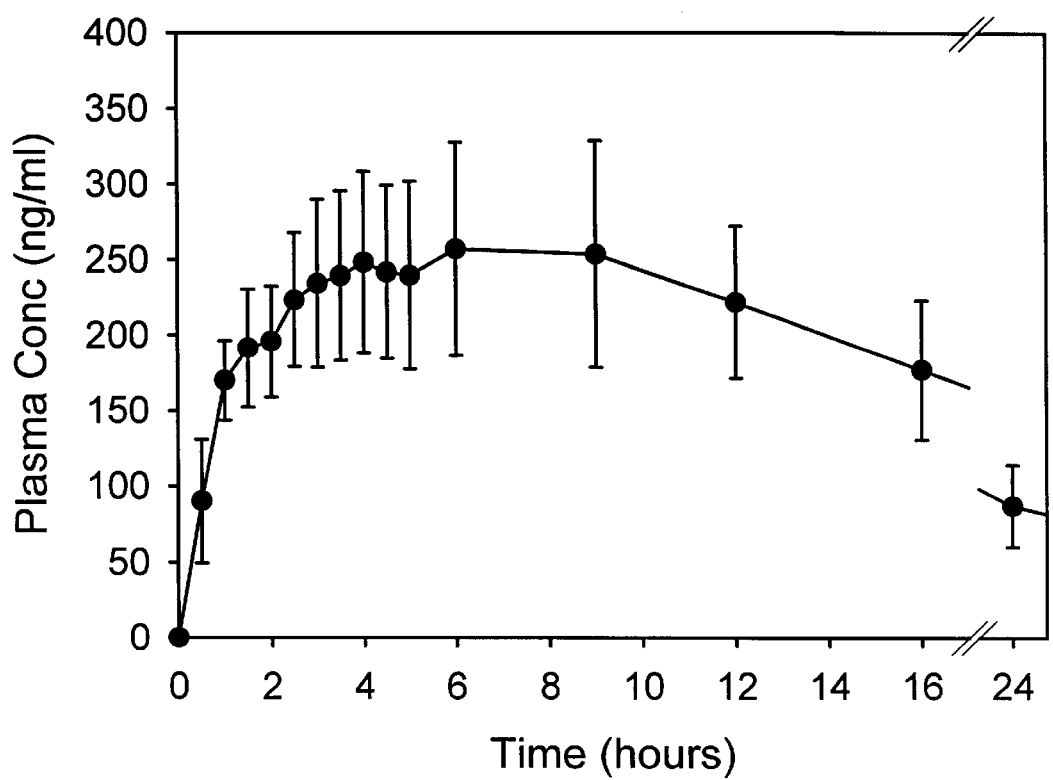
FIG. 5: Human pharmacokinetics of tablets LP-1473 (with film coating).

The plasma concentration curves for tramadol, as indicators of the release profile of these tablets are illustrated in FIG. 4 and FIG. 5.

The release profile of tablets LP-1443, containing 100 mg of tramadol, was equivalent to Tramal Long 100®.

For LP-1473 tablets (with film coating) containing 200 mg of tramadol, the targeted sustained release profile was attained, with plasma concentrations in the 100 to 300 ng/mL range from around 30 min to around 24 hours post-dose.

Example 9

Robustness Evaluation

Robustness is defined as a limited dependence of dissolution profile of active ingredient upon changes in the production or dissolution testing conditions. All tests for robustness were conducted on a Vankel BioDiss (U.S.P. type III) dissolution test station. To test under dissolution conditions for robustness evaluation, the BioDis was configured with two rows of dissolution vessels. The vessels were filled each with 250.0 g of dissolution medium. The dissolution medium was either U.S.P. standard buffer pH 1.2, U.S.P. standard buffer pH 6.8 (50 mM), or U.S.P. standard buffer pH 7.5 (50 mM). The enzyme used was α-Amylase Bacillus from Sigma Chemicals. The cells containing the tablets were fitted with a 40 mesh screen in the lower caps and a 20 mesh screen in the upper caps. Dissolution tests were conducted at 37° C. for 24 hours. The method used is outlined below for each of the individual tests.

Tests: pH 1.2, pH 6.8 (without enzyme), and pH 7.5:

| TIME (hours) | Dissolution medium | Agitation (dips/min) |
|---|---|---|
| 05:00 | pH 1.2, or 6.8, or 7.5 | 15 |
| 19:00 | | 5 |

Tests: pH 6.8+4500 IU/L (or 18000 IU/L):

| TIME (hours) | Enzyme (I.U./L) | Agitation (dips/min) |
|---|---|---|
| 05:00 | 4500 or 18000 | 15 |
| 19:00 | | 5 |

Tests: agitation 5 dips/min, 15 dips/min:

| TIME (hours) | Dissolution medium | Agitation (dips/min) |
|---|---|---|
| 05:00 | pH 6.8 without enzyme | 5 or 15 |
| 19:00 | pH 6.8 without enzyme | 5 or 15 |

Each dissolution medium was sampled at specific time points. Each aliquot was filtered through a 2 mm filter (Millex AP) prior to assay using a UV-Visible spectrophotometer (see Example 6). The dissolution profiles of LP-1443, LP-1473 (without film coating) under various pH, agitation, and enzymatic conditions were obtained.

Figure 6:
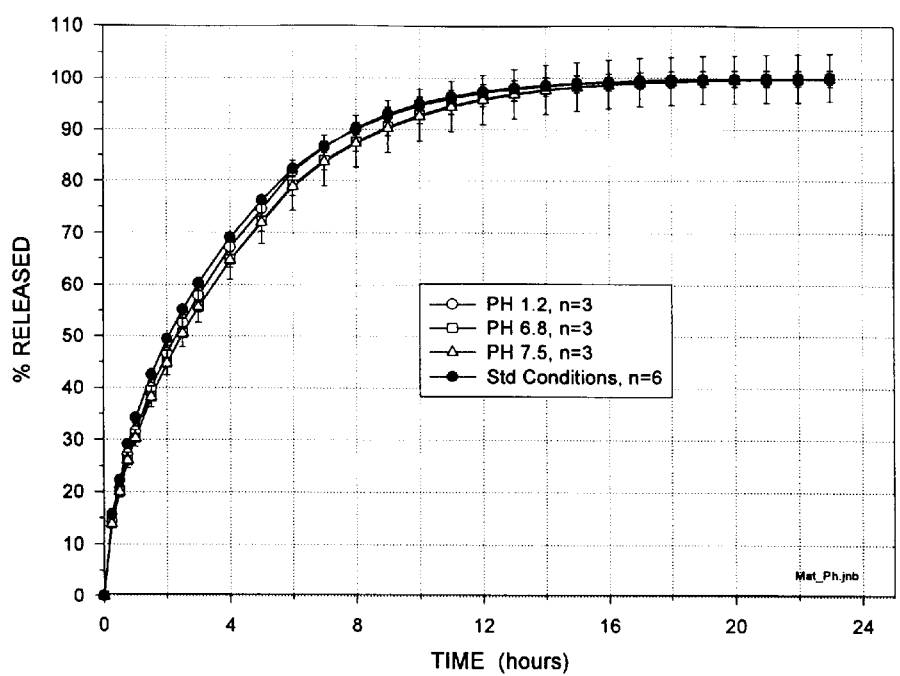
FIG. 6: Effect of pH of dissolution medium on the dissolution profile of formulation LP-1443.

FIG. 6 shows that variation of dissolution medium pH had no significant effect on the release profile of formulation LP-1443.

Figure 7:
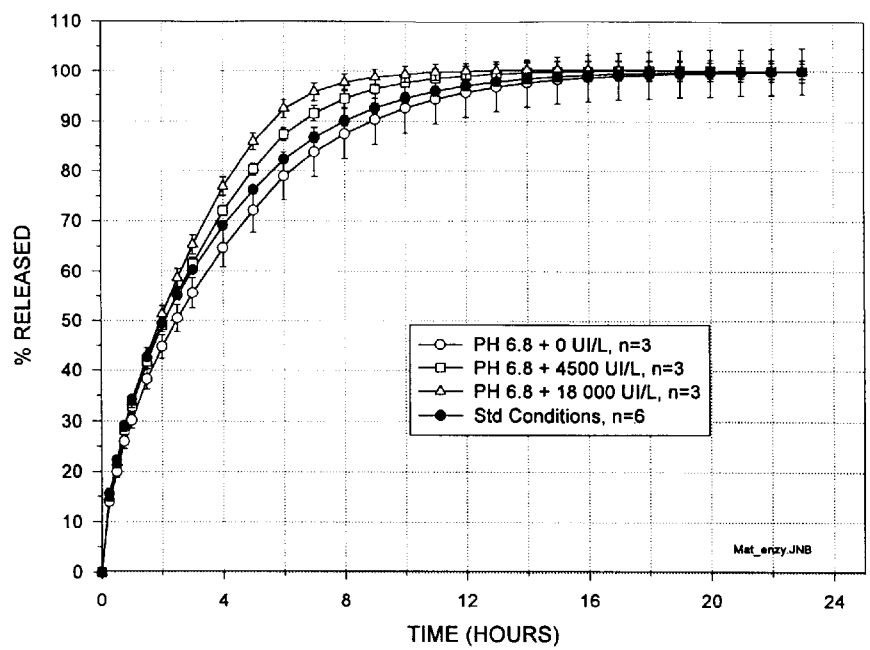
FIG. 7: Effect of α-Amylase Bacillus in dissolution medium on the dissolution profile of formulation LP-1443.

FIG. 7 shows the effect of enzyme on the dissolution profile. Whilst the release profiles under standard dissolution conditions and at pH 6.8 are comparable, the release rate increased marginally when the enzyme was used throughout the test. This increase appeared to be dependent upon enzyme concentration.

Figure 8:
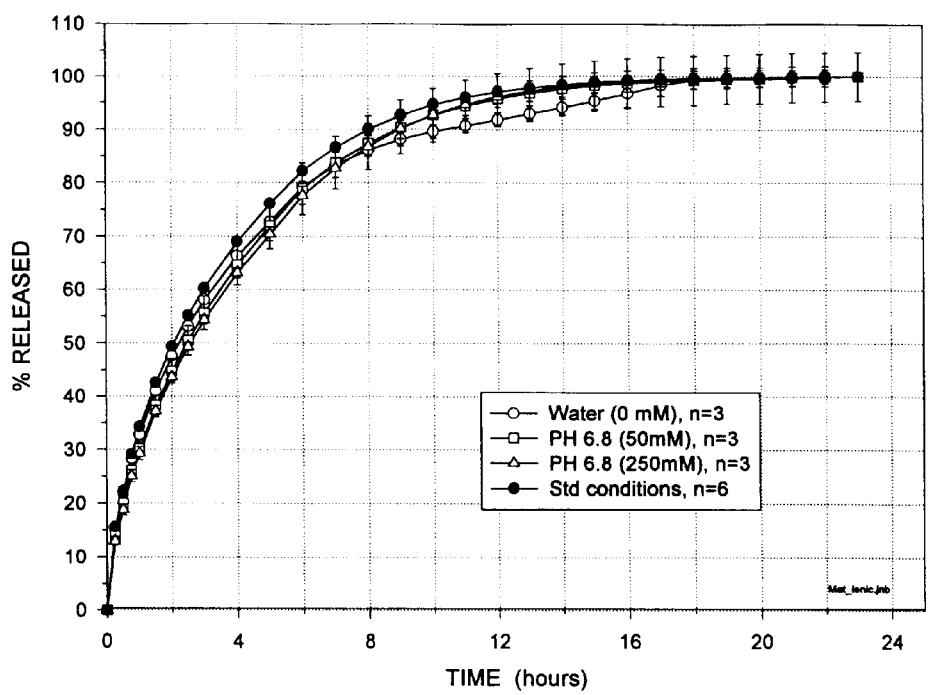
FIG. 8: Effect of dissolution medium ionic strength on the dissolution profile of formulation LP-1443.

FIG. 8 shows that variation of dissolution medium ionic strength had no significant effect on the release profile of formulation LP-1443.

Figure 9:
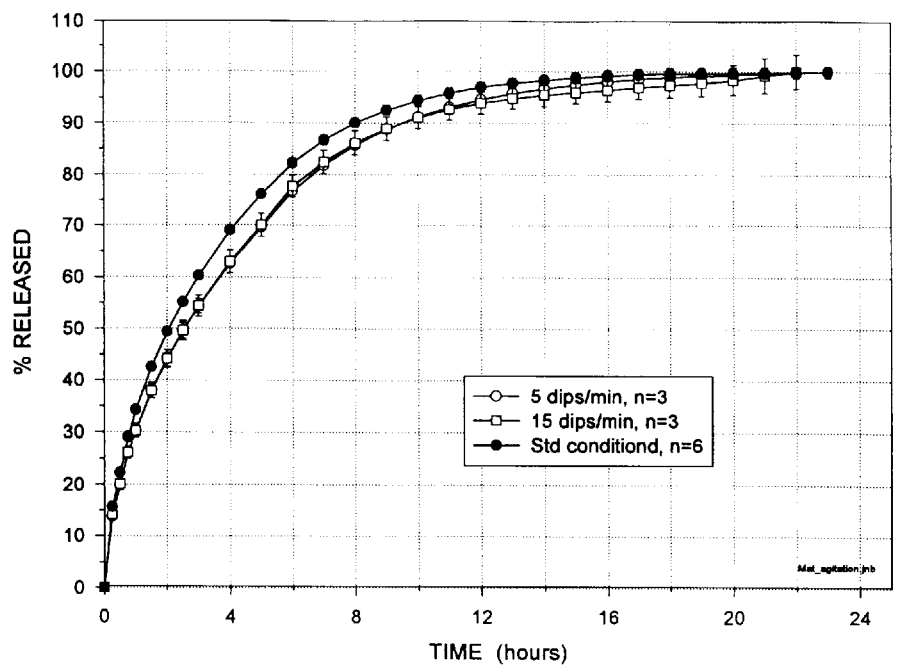
FIG. 9: Effect of agitation rate on the dissolution profile of formulation LP-1443.

FIG. 9 shows that variation in the rate of agitation during dissolution had no effect within the range tested.

Figure 10:
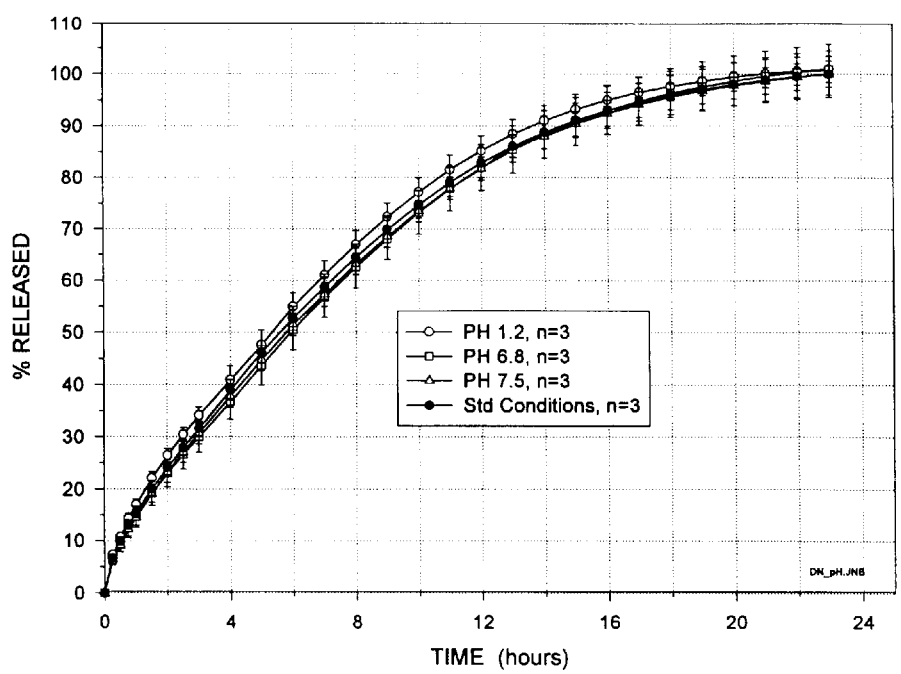
FIG. 10: Effect of pH of dissolution medium on the dissolution profile of formulation LP-1473 (without film coating).

FIG. 10 shows the dissolution profiles of formulation LP-1473 (without film coating) at different pH values. The dissolution profiles at pH 1.2, pH 6.8 or pH 7.5 were not significantly different from that under standard conditions.

Figure 11:
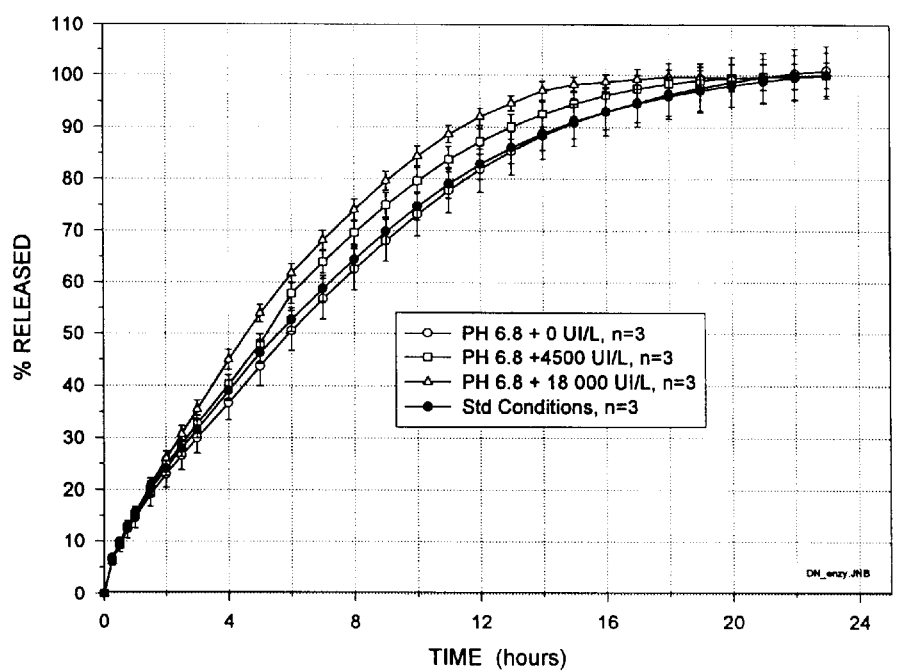
FIG. 11: Effect of α-Amylase Bacillus in dissolution medium on the dissolution profile of formulation LP-1473 (without film coating).

FIG. 11 shows the effect of enzyme on the dissolution profile. Whilst the release profiles under standard dissolution conditions and at pH 6.8 are comparable, the release rate increased marginally and non-significantly when the enzyme was used throughout the test. This increase appeared to be dependent upon enzyme concentration.

Figure 12:
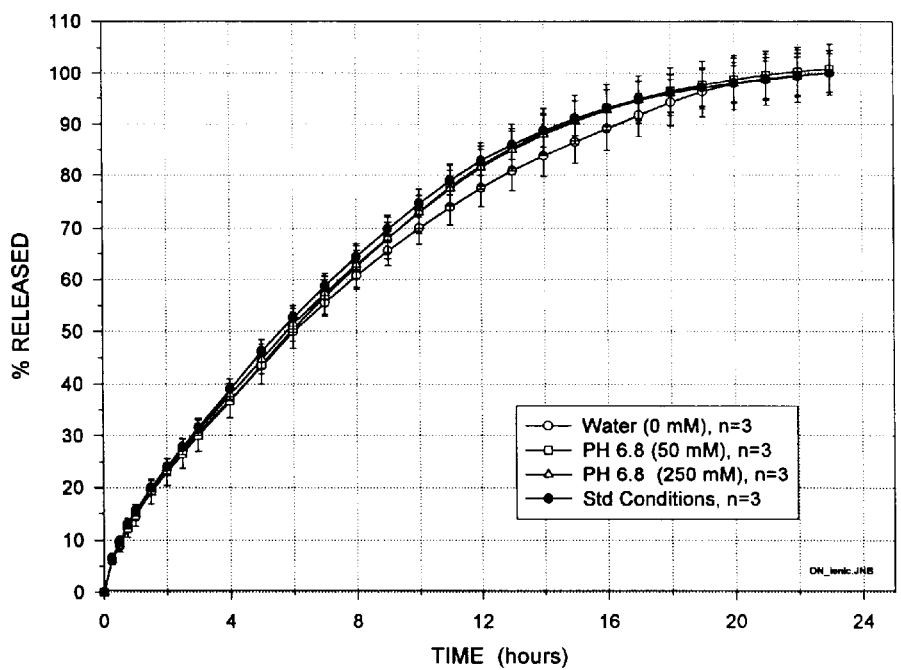
FIG. 12: Effect of dissolution medium ionic strength on the dissolution profile of formulation LP-1473 (without film coating).

FIG. 12 shows that variation of dissolution medium ionic strength had no significant effect on the release profile of formulation LP-1473 (without film coating).

Figure 13:
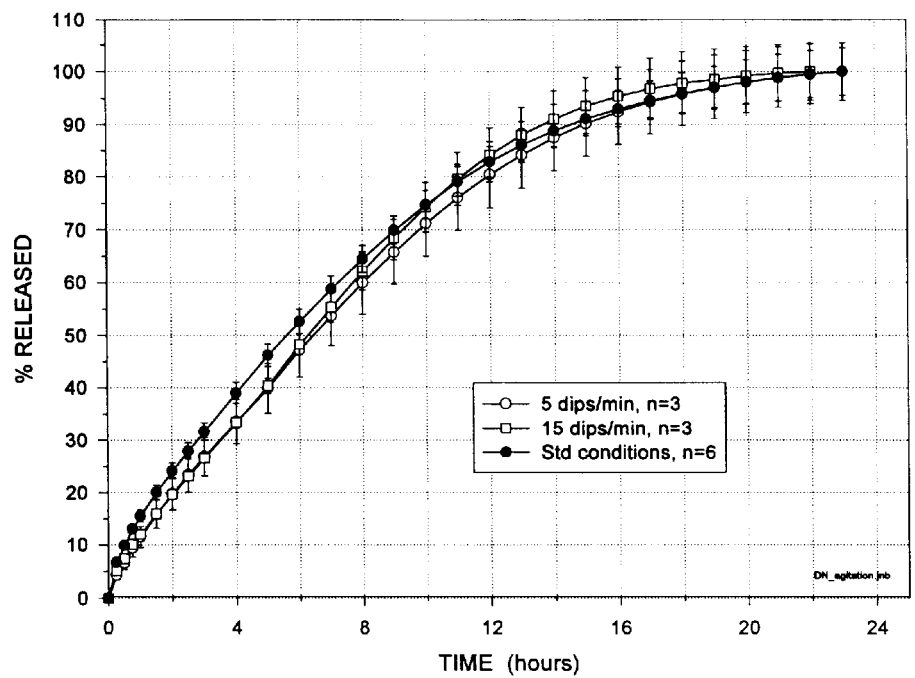
FIG. 13: Effect of agitation rate on the dissolution profile of formulation LP-1473 (without film coating).

FIG. 13 shows that variation in the rate of agitation during dissolution had no effect on formulation LP-1473 (without film coating) within the tested range.

Example 10

Rheological Observation on Swollen Cross-linked Starches

Cross-linked high amylose starch (CLHAS) made by the process of the present invention as disclosed in Example 1 (Cerestar) is different from that made by the process disclosed by Rougier (Rougier) in Dumoulin et al. WO 98/35992. When swollen in water, the Cerestar tablets swell about 20% in width and 79% in thickness, compared to the 29% and 72%, respectively for the Rougier tablet. After uptaking water, the Cerestar tablets has a weight increase of 2.55 times the original weight of the dry Cerestar tablet. Rougier tablets increase weight by 3.11 times of the dry Rougier tablets. The effect of temperature on swelling is less pronounced for the Cerestar tablet, i.e., water uptake increment is less than for the Rougier tablets.

Figure 14:
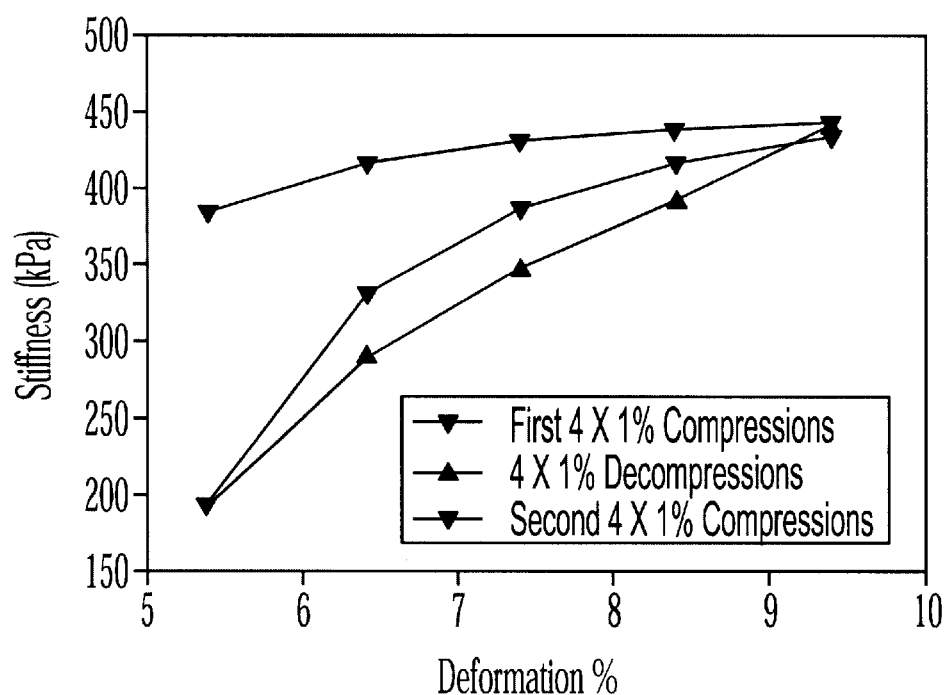
FIG. 14: Quasi-reversible visco-elastic properties of Cerestar tablet.
Figure 15:
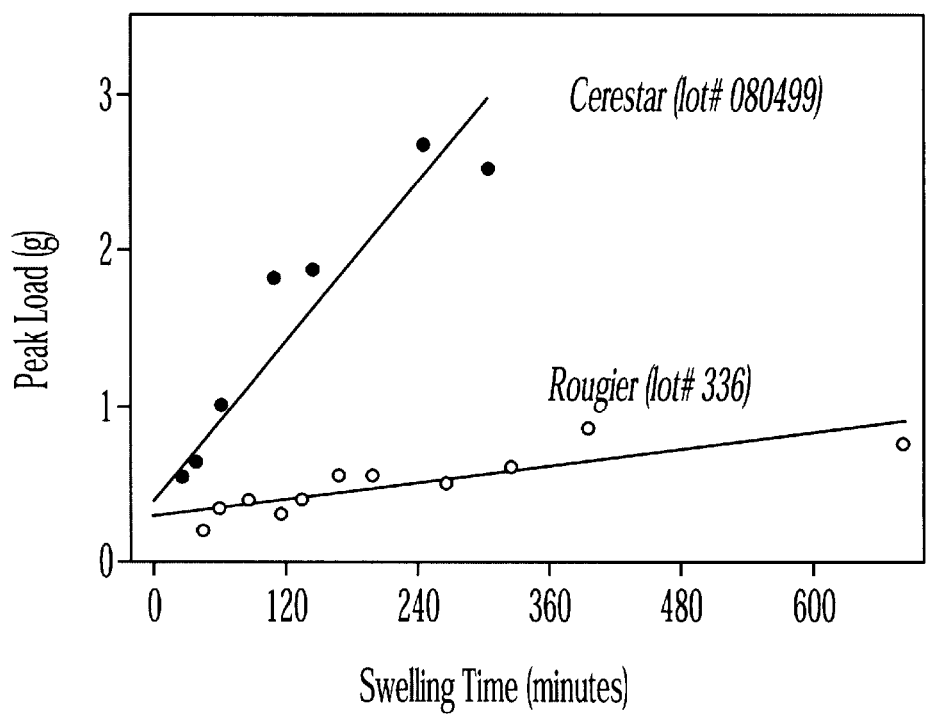
FIG. 15: Stress-relaxation curves obtained from the 1% strain step application.

Comparing the swelling behavior of a Cerestar and a Rougier tablets that have the same thickness reveals that Cerestar tablets demonstrate a more rapid increase in stiffness when plunged in water (FIG. 14). At different intervals of time, a compression of 1% was applied to the tablets and only the peak load was recorded. Afterward, the tablet was allowed to reswell to equilibrium in an unconfined state. Experiments were conducted on a Mach-1™ instrument with tablets of 3 mm thickness. Stress-relaxation curves (FIG. 15) obtained from the 1% strain step application indicate that the Cerestar tablets are much stiffer than the Rougier tablets, i.e. Cerestar tablets have more pronounced resistance to a 1% strain compression. Cerestar tablets exhibit a peak resistance about 1.5 times bigger than for the Rougier tablets (from about 15 g to 25 g load per 1% compression).

Example 11

SEM Micrographs of Water Swollen Cerestar and Rougier Tablets

Figure 16:
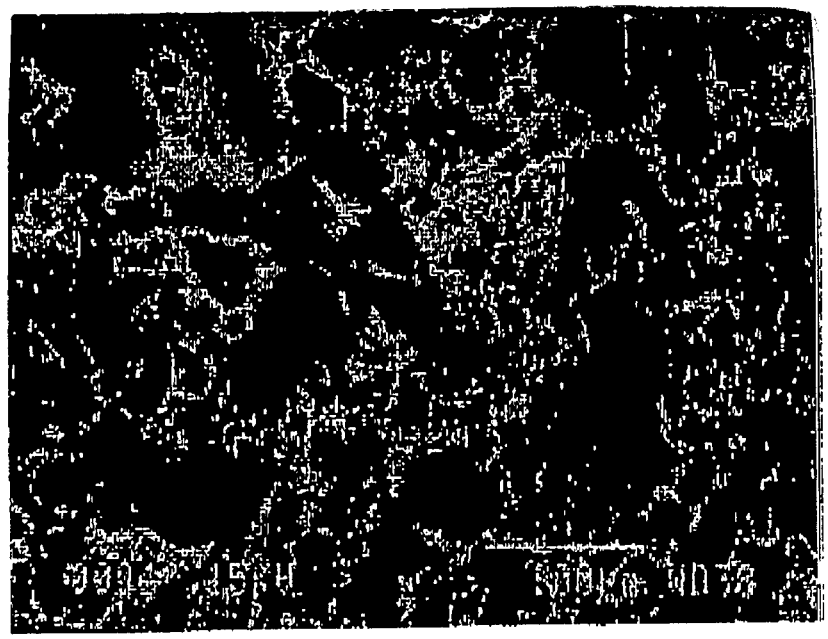
FIG. 16: SEM: Surface of free-dried Cerestar water swollen tablet.
Figure 17:
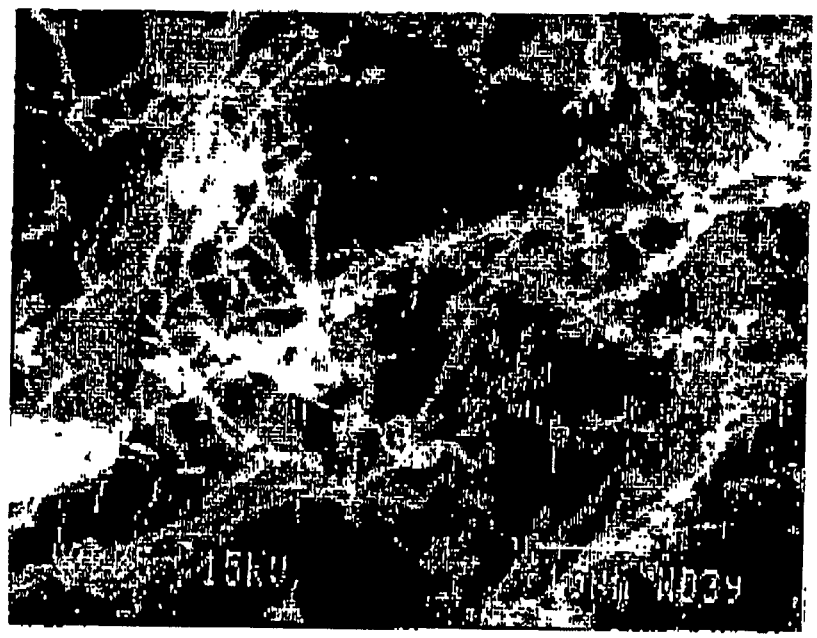
FIG. 17: SEM: Freeze-dried supernatant suspension present around a water swollen Cerestar tablet.
Figure 18:
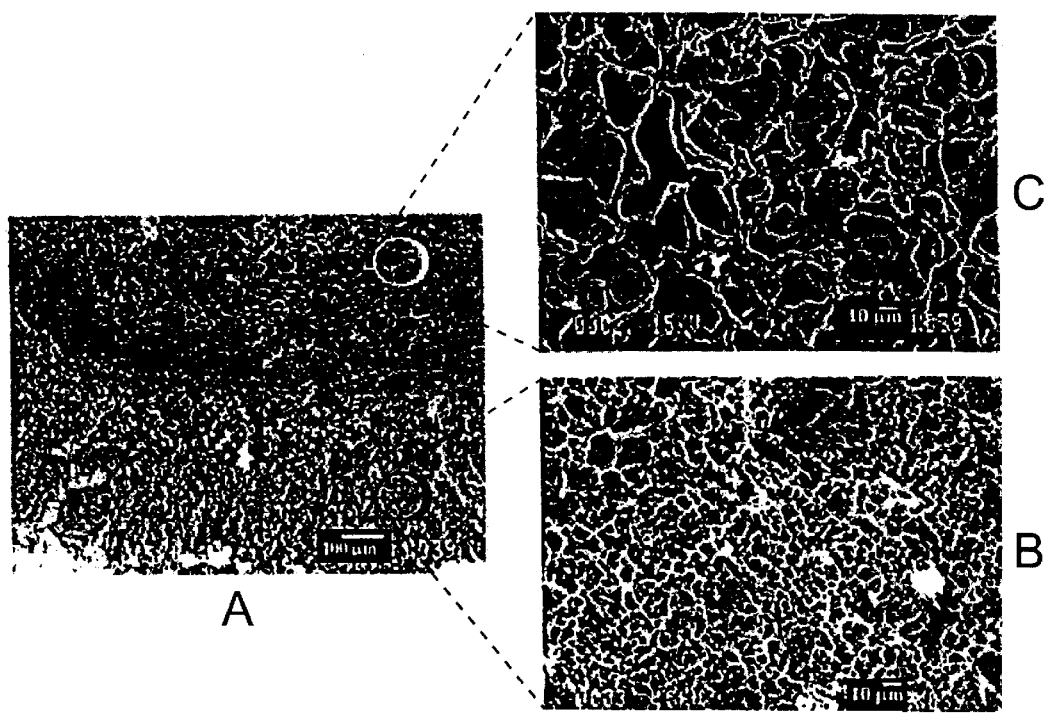
FIG. 18: SEM: Rougier tablets at equilibrium swelling in water at 37° C.

Scanning Electron Microscope (SEM) technique was used to examine the morphology of Cerestar and Rougier tablets and revealed a great distinction between the two. FIG. 16 shows the SEM micrographs of the surface of freeze-dried Cerestar water swollen tablet. FIG. 17 shows the SEM micrographs of freeze-dried supernatant suspension present around a water swollen Cerestar tablet. For comparison, FIG. 18 show the SEM of Rougier tablets at equilibrium swelling in water at 37° C.

Example 12

Gel Permeation Chromatography Analysis

Five starch samples:(1) C Amylogel03003 HA Starch is the 70% amylose starch which is the a raw material for Cerestar, (2) Contramid Lot 333 is crosslinked HA starch made by the Rougier process, (3) Cerestar modified HA starch batch 1903 (manufactured as disclosed in Example 1), (4) Cerestar modified HA starch batch HE 3825 (manufactured as disclosed in Example 1), and (5) Cerestar modified HA starch batch HE 3808 (manufactured as disclosed in Example 1) were analyzed by gel permeation chromatography (GPC).

GPC analysis was conducted in the following 4 steps:
1) Dissolution of the samples in 90% DMSO (15 mg/ml, 3days at 80° C.) and dilution of the solution with lubricant (0.005M $Na_2CO_3$)2:1);
2) Fractioning of the samples on column system I (Sephacryl-columns). Sample volume: 1.6 ml;
3) Analysis of the fractions on iodine coloring (640 nm and 525 nm) and total carbohydrate; and
4) Calibration of the column system with a widely dispersed molecule standard (BDS-HES).

GPC results for each of the five samples are as follows:
(1) C AmylogelGel 03003 HA Starch (Amylogel 3003)

It contains ca. 20% high molecular parts, ration 640/525 nm between 0.4 and 0.6, which correspond to amylopectin structures. The low molecular parts have their elution maximum at the fraction 90, whereas the molecular scale here is 300000 Dalton [g/M]. From the ratio 640/525 nm it is clear that there are differently branching structures, in the maximum the ratio is between 1.6 and 2, which corresponds to long chain branched structures.

(2) Rougier Lot 333

This starch product has very wide dispersion with parts of different structural composition. A bigger proportion of high molecular components contains a ratio b 640/525nm at 1 (ca. 50%). The low molecular part contains a high proportion of differently branching structures where a ratio between 1.2 and 1.6 can be observed.

(3) Cerestar Modified HA starch (Batch 1903)

This modified HA starch has wide molecular dispersion, in which the proportion of high molecular components is relatively small, and the ratio 640/525 nm is between 1 and 1.6. The iodine coloring indicates branched structures with medium length of segments.

(4) Cerestar Modified HA starch (Batch 3825)

This modified starch also consists of wide molecular dispersion, where the proportion of high molecular components is significantly higher. The iodine coloring shows similar structure characteristics, the ratio 640/525 nm is of the same scale between 1 and 1.6.

(5) Cerestar Modified HA starch (Batch 3808)

High molecular components are missing in this batch. The proportion of low molecular components is significantly higher than that of Batch 1903 and 3825. The found values for the ratio 640/525 nm are very much uniform in the scale of 1.5, which indicates equally branched structures with medium branched segment length.

Figure 19:
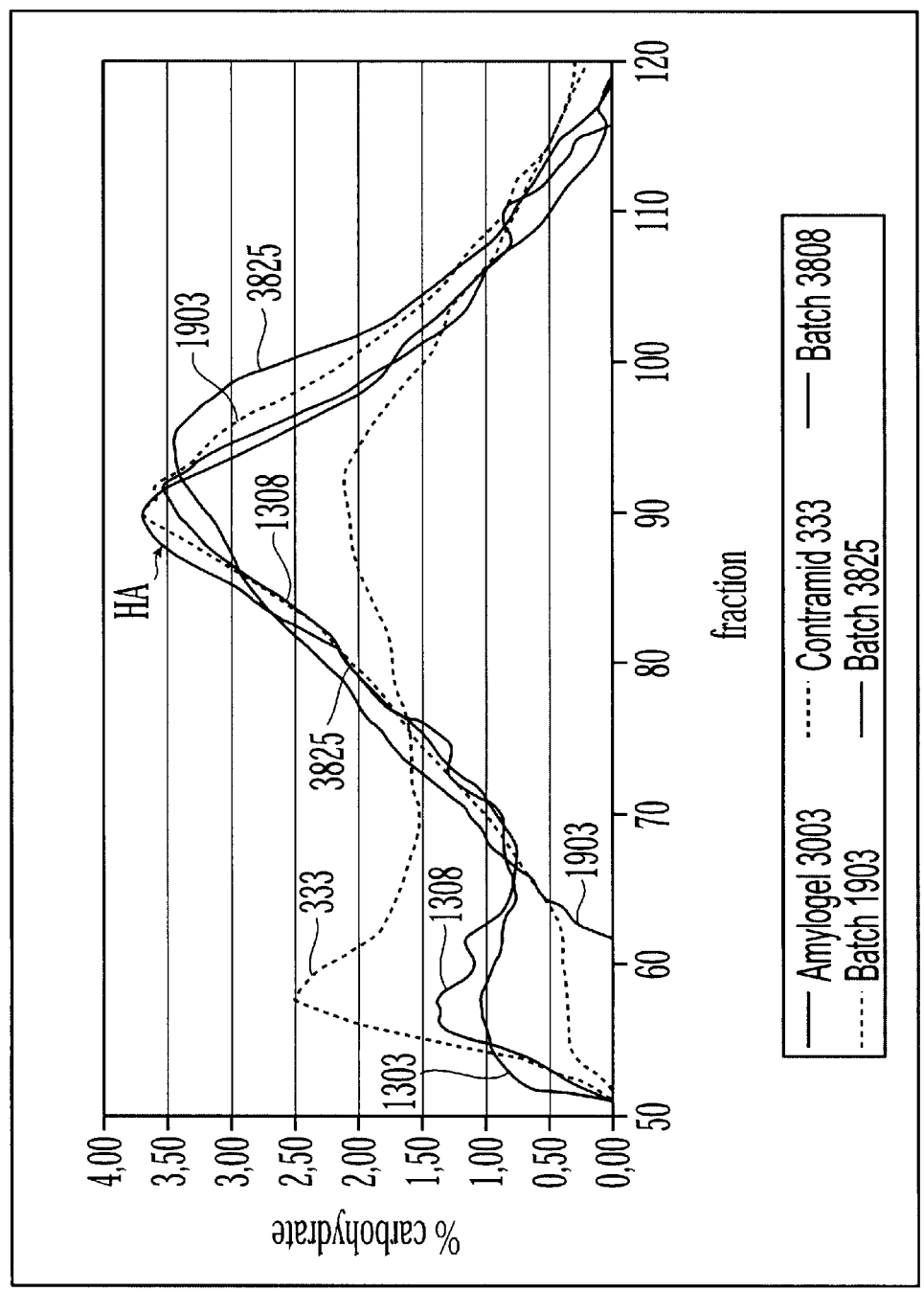
FIG. 19: GPC result, % carbohydrate in Amylogel 3003, Contramid-Rougier 333, Cerestar Batches 3808, 1903, 3825; as a function of fraction.
Figure 20:
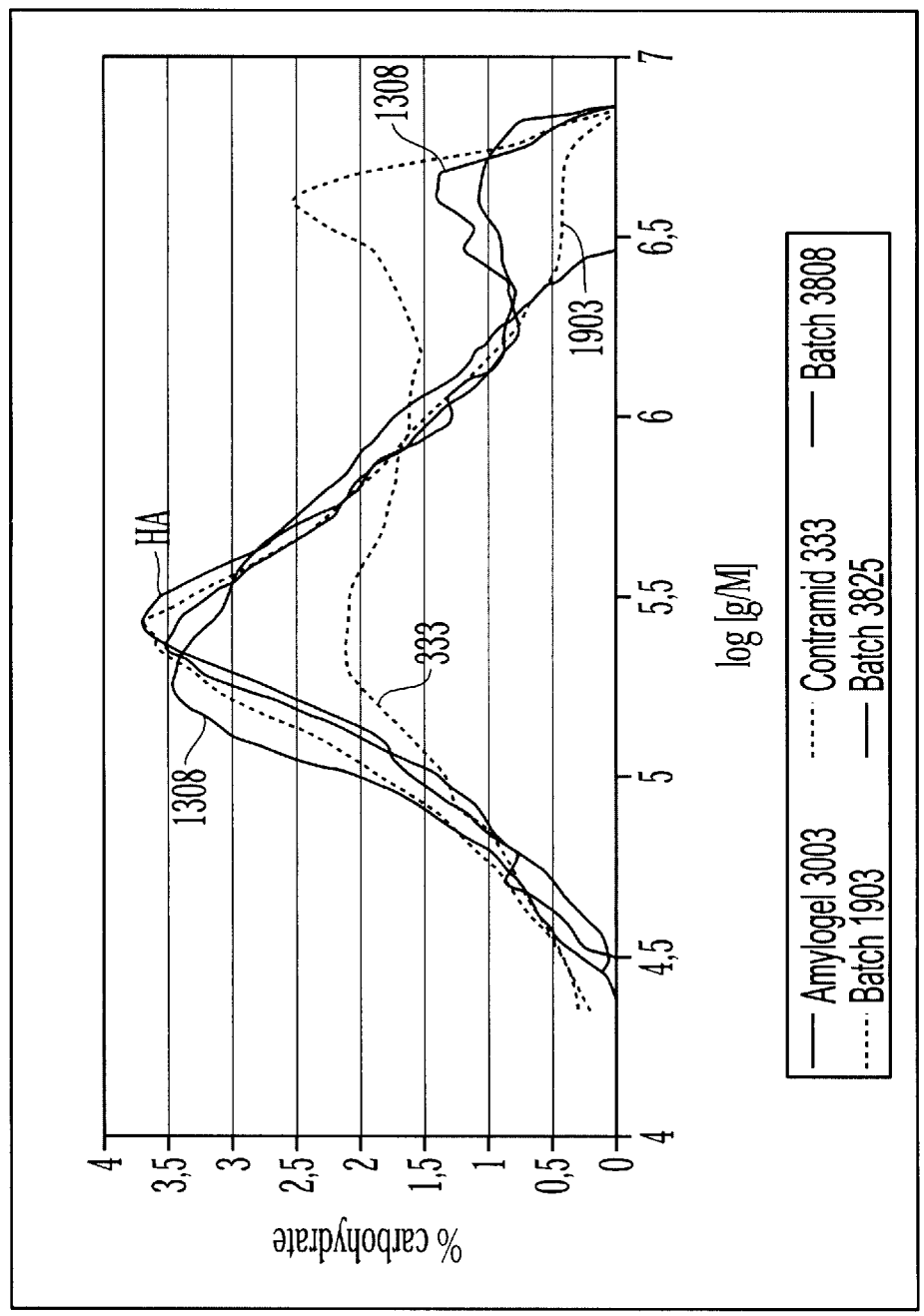
FIG. 20: GPC result, % carbohydrate in Amylogel 3003, Contramid-Rougier 333, Cerestar Batches 3808, 1903, 3825; as a function of log [g/M].

The marked difference between crosslinked HA starch made by the Rougier process (contramid (Rougier) 333) and those by the process of the present invention (Batch 3808, 1903, 3825) are illustrated in FIGS. 19 and 20. In the Rougier product, a significant amount of amylose has been eluted together with amylopectin indicating that covalent links were created by the chemical treatment. In the Cerestar products, the peak at high molecular weight is smaller, which may result from a breakdown of the amylopectin in smaller subunits. The quantity of amylose bound to amylopectin is smaller than in the Rougier. This may be due to either the fact that cross-linking takes place preferentially between amylose molecules rather than between amylose and amylopectin or that the degree of cross-linking is lower (Cerestar uses 0.075% phosphorus oxychloride whereas Rougier uses 3.25% sodium trimetaphosphate).

Example 13

Preparation of Implants

Dry blends of cross-linked high amylose starch, Lubritab® (Penwest Pharmaceuticals Co.) and Ciprofloxacin HCl were prepared with the following compositions:

|  | Type A (2.5% Ciprofloxacin HCl) | Type B (5% Ciprofloxacin HCl) | Type C (7.5% Ciprofloxacin HCl) |
| --- | --- | --- | --- |
| cross-linked high amylose starch | 97% | 94.5% | 92% |
| Ciprofloxacine HCl | 2.5% | 5.0% | 7.5% |
| Lubritab ® | 0.5% | 0.5% | 0.5% |

These blends were compressed using a 7.1 mm round-punch to provide 5 mm thick implants in the form of a tablet. The weight of each of the tablets formed (Type A, or B, or C) is 200 mg.

Example 14

In Vitro Drug Release of Implants

Experiments were carried out over 21 days with 2.5%, 5% and 7.5% Ciprofloxacin HCl (Cipro) implants (Type A, Type B, Type C as described in Example 13, respectively) individually immersed in 20 mL of isotonic phosphate buffered saline (PBS), pH 7.4. Watertight vessels were maintained at 37° C. in a shaking bath. Implants were transferred into 20 mL of fresh PBS every 24 hours. Ciprofloxacin HCl was assayed by UV spectrometry (277 nm).

Figure 21:
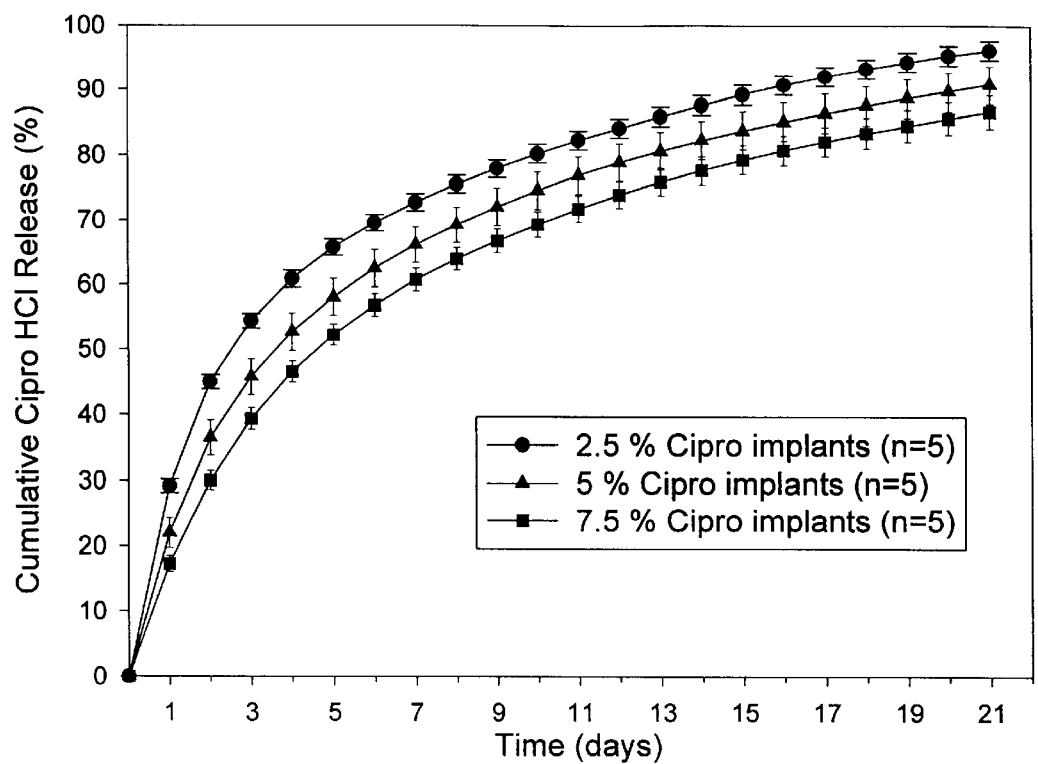
FIG. 21: In vitro cumulative Ciprofloxacin HCl release with 3 different implant loadings.

As shown in FIG. 21, Ciprofloxacin HCl release was obtained over 21 days with a good reproducibility. Surprisingly, Ciprofloxacin HCl initial release rate decreased with increasing drug loading.

Example 15

In Vivo Study of Implants

Eighteen 2 kg New Zealand white rabbits were used to evaluate systemic and local antibiotic release of Ciprofloxacin HCl from implants. Animals were randomly allotted into two groups (2.5% and 7.5% Ciprofloxacin HCl). The right hind leg was aseptically prepared for each rabbit. Skin and lateral femoral fascia were incised to expose femur diaphysis. Each rabbit was given 30 mg of Ciprofloxacin HCl, in the form of cross-linked high amylose starch implants (either type A or C, as described in Example 13). The implants were placed between quadriceps and femur and then the fascia and skin were sutured. Animals were monitored daily. Euthanasia was performed on days 3, 7, 14, 21 and 28 post-implantation. Quadriceps and femur were collected for Ciprofloxacin HCl assay and histology examination. Blood samples were taken on days 0, 1, 2, 3, 5, 7, 10, 14, 21 and 28 on all remaining animals for Ciprofloxacin HCl assay by HPLC.

As an implantable form, the good biocompatibility of cross-linked high amylose starch upon subcutaneous implantation had already been demonstrated in rats (C. Désévaux, et al. Proceed. Int'l. Symp. Control. Rel. Bioact. Mater. 26 (1999) 635–636). Likewise, in this study in rabbits, no adverse local reaction nor health effect occurred. Post-mortem macroscopic inflammation was slight and limited to implantation sites. Heterophils and macrophages were observed inside and around cross-linked high amylose starch implants, respectively.

Figure 22:
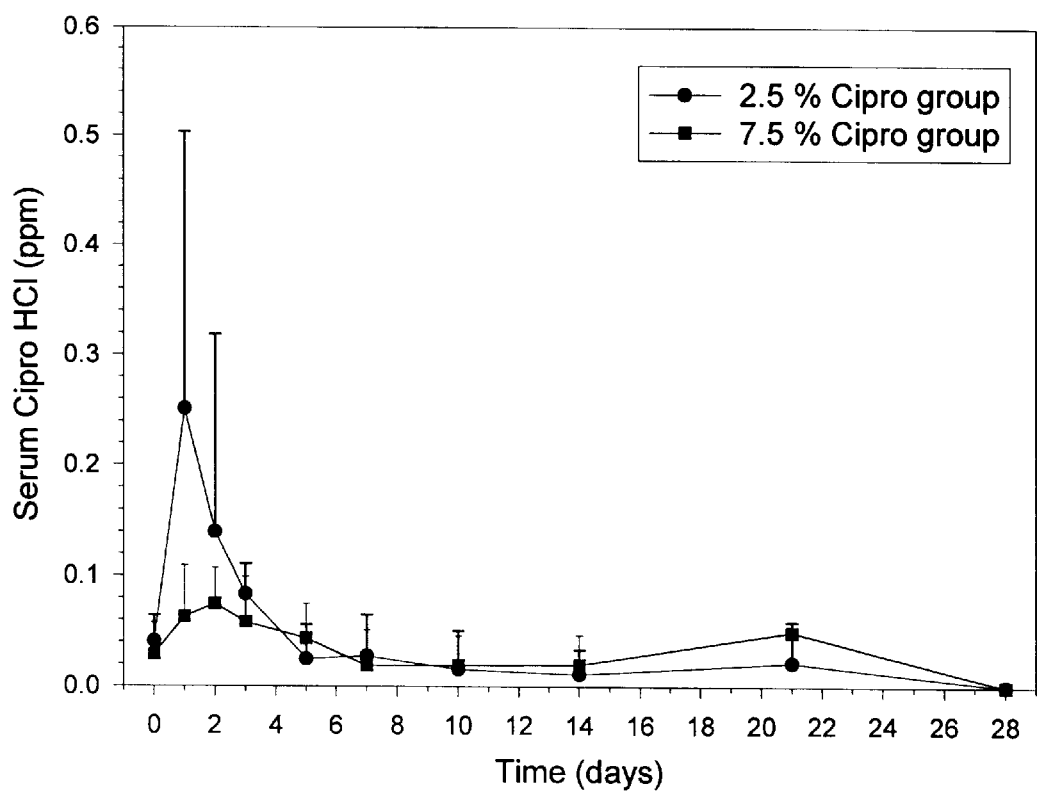
FIG. 22: Serum Ciprofloxacin concentrations.

As shown in FIG. 22, serum Ciprofloxacin HCl was always detected at a low level until day 21 limiting the possibility of toxic effects. In line with in vitro data, initial release was more controlled and reproducible with Ciprofloxacin HCl implants type C.

Figure 23:
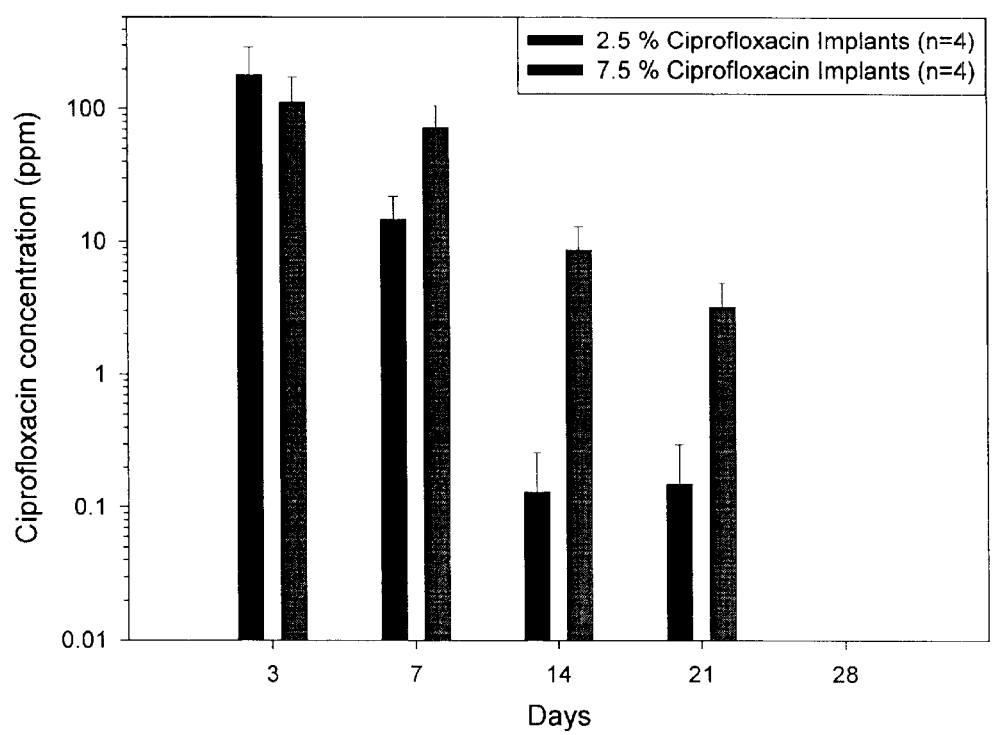
FIG. 23: Muscle Ciprofloxacin concentrations.

As shown in FIG. 23, elevated antibiotic levels were found in the muscles over a long period (21 d) with C type implants. In line with the in vitro data, the local concentrations following implantation of the A implants were lower after 14 days.

In conclusion, the type C implants can be used safely and efficiently for the local treatment or prevention of bone infection, such as for example after a trauma or following a surgical procedure.

While it is apparent that the embodiments of the invention herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present invention.

A number of references have been cited and the entire disclosures of which are incorporated herein by reference.

We claim:

1. A process for manufacturing, in an aqueous medium, a controlled release excipient consisting primarily of cross-linked high amylose starch, for use in preparation of tablets, said process comprising (a) cross-linking high amylose starch thereby forming a reaction medium containing a reaction product consisting of a cross-linked high amylose starch slurry;

(b) subjecting said cross-linked high amylose starch slurry from step (a) to chemical modification at a temperature of about 10 to about 90° C. for about 1 to about 72 hours;

(c) neutralizing said reaction medium obtained in step (b) with an acid, washing the slurry formed and optionally dewatering or to form a starch cake or a dry powder;

(d) diluting said slurry or re-slurrifying said starch cake or said dry powder from step (c) with water to form a slurry at a concentration of about 2% to about 40% w/w, adjusting pH to a desired value between about 3 and about 12, and gelatinizing said slurry at a temperature of about 80 to 180° C. for about 1 second to about 120 minutes; and (e) drying the thermally treated product obtained in step (d) to obtain said controlled release excipient consisting mainly of chemically modified and cross-linked high amylose starch in form of a powder.

2. The process according to claim 1, wherein steps (a) and (b) are performed at the same time.

3. The process according to claim 1 comprising, (a) cross-linking high amylose starch containing at least 70% w/w of amylose with about 0.005 g to about 0.3 g cross-linking reagent per 100 g of dry-based high amylose starch in an aqueous medium at a temperature of about 10 to about 90° C. thereby forming a reaction medium containing a reaction product consisting of a cross-linked high amylose starch slurry;

(b) subjecting said cross-linked high amylose starch slurry from step (a) to hydroxypropylation with propylene oxide at a temperature of about 10 to about 90° C. for about 1 to about 72 hours to yield a reaction medium containing a hydroxypropylated cross-linked high amylose starch slurry;

(c) neutralizing said reaction medium obtained in step (b) with a dilute aqueous acid, washing slurry formed and optionally dewatering to obtain a starch cake or a dry powder;

(d) diluting said slurry, or re-slurrifying starch cake or dry powder from step (c) with water to form a slurry at a concentration of about 2% to about 40% w/w, adjusting pH to about 4.0 to about 9.0, and gelatinizing said slurry formed in current step at a temperature of about 80 to about 180° C. for about 1 second to about 120 minutes; and (e) drying said thermally treated product obtained in step (d) to obtain said controlled release excipient consisting mainly of hydroxypropylated and cross-linked high amylose starch in form of a powder.

4. The process of claim 3, wherein, in step (a), said cross-linking reagent is phosphorous oxychloride in an amount of between about 0.01 and about 0.2 g per 100 g starch dry basis or sodium trimetaphosphate in an amount of between about 0.05 and about 0.3 g per 100 g starch dry basis.

5. The process of claim 3 wherein step (a) is performed in an aqueous alkaline medium.

6. The process of claim 4, wherein, in step (a), said cross-linking is carried out at a pH of about 10 to about 14 and at a temperature of about 15 to about 90° C. for about 0.2 to about 40 hours.

7. The process of claim 3, wherein, in step (b), said hydroxypropylation is carried out with up to 10% propylene oxide at a temperature of about 40 to about 80° C. for about 10 to about 72 hours.

8. The process of claim 3, wherein, in step (c), said neutralization of said reaction medium is carried out with dilute sulfuric acid or hydrochloric acid.

9. The process of claim 3, wherein, in step (d), said gelatinization is carried out by direct steam injection into an aqueous suspension of said cross-linked high amylose starch.

10. The process of claim 3, wherein, in step (d), said pH is adjusted to about 6.0 and said temperature is kept at about 80 to about 180° C. for about 2 to about 10 minutes.

11. The process of claim 3, wherein, in step (e), said drying is carried out by spray-drying.

12. The process of claim 11, wherein, in step (e), inlet temperature is from about 60 to about 350° C., and outlet temperature is set from about 40 to about 210° C.

13. A process for manufacturing, in an aqueous medium, a controlled release excipient consisting primarily of cross-linked high amylose starch, for use in preparation of tablets, said process comprising (a) subjecting high amylose starch to chemical modification at a temperature of about 10 to about 90° C. for about 1 to about 72 hours thereby forming a reaction medium containing a chemically modified high amylose slurry;

(b) cross-linking said chemically modified high amylose starch in said slurry obtained in step (a);

(c) neutralizing said slurry obtained in step (b) with an acid, washing the slurry formed and optionally dewatering to form a starch cake or drying to form dry powder;

(d) diluting said slurry, or re-slurrifying said starch cake or said dry powder from step (c) with water to form a slurry at a concentration of about 2% to about 40% w/w, adjusting pH to a desired value between about 3 and about 12, and gelatinizing said slurry at a temperature of about 80 to 180° C. for about 1 second to about 120 minutes; and (e) drying the thermally treated product obtained in step (d) to obtain said controlled release excipient consisting mainly of chemically modified and cross-linked high amylose starch in form of a powder.

14. The process according to claim 13, wherein steps (a) and (b) are performed at the same time.

15. The process according to claim 13 comprising (a) subjecting high amylose starch containing at least 70% w/w of amylose to hydroxypropylation With propylene oxide at a temperature of about 10 to about 90° C. for about 1 to about 72 hours to yield a reaction medium containing a reaction product of consisting primarily of a hydroxypropylated high amylose starch slurry;

(b) cross-linking said hydroxypropylated high amylose starch slurry with about 0.005g to about 0.3 g cross-linking reagent per 100 g of dry-based high amylose starch in an aqueous medium at a temperature of about 10 to about 90° C. to yield a reaction medium containing a cross-linked hydroxypropylated high amylose starch slurry;

(c) neutralizing said reaction medium obtained in step (b) with a dilute aqueous acid, washing slurry formed and optionally dewatering to obtain a starch cake or a dry powder;

(d) diluting said slurry, or re-slurrifying said starch cake or said dry powder from step (c) with water to form a slurry at a concentration of about 2% to about 40% w/w, adjusting pH to about 4.0 to about 9.0, and gelatinizing said slurry formed in current step at a temperature of about 80 to about 180° C. for about 1 second to about 120 minutes; and (e) drying said thermally treated product obtained in step (d) to obtain said controlled release excipient consisting mainly of hydroxypropylated and cross-linked high amylose starch in form of a powder.

16. All The process of claim 15, wherein, in step (a), said cross-linking reagent is phosphorous oxychloride in an amount of between about 0.01 and about 0.2 g per 100 g starch dry basis or sodium trimetaphosphate in an amount of between about 0.05 and about 0.3 g per 100 g starch dry basis.

17. The process of claim 15 wherein step (b) is performed in an aqueous alkaline medium.

18. The process of claim 16, wherein, in step (b), said cross-linking is carried out at a pH of about 10 to about 14 and at a temperature of about 15 to about 90° C. for about 0.2 to about 40 hours.

19. The process of claim 15, wherein, in step (a), said hydroxypropylation is carried out with up to 10% propylene oxide at a temperature of about 40 to about 80° C. for about 10 to about 72 hours.

20. The process of claim 15, wherein, in step (c), said neutralization of said reaction medium is carried put with dilute sulfuric acid or hydrochloric acid.

21. The process of claim 15, where, in step (d), said gelatinization is carried out by direct steam injection into an aqueous suspension of said cross-linked high amylose starch.

22. The process of claim 15, wherein, in step (d), said pH is adjusted to about 6.0 and said temperature is kept at about 80 to about 180° C. for about 2 to about 10 minutes.

23. The process of claim 15, wherein, in step (e), said drying is carried out by spray-drying.

24. The process of claim 23, wherein, in step (e), inlet temperature is from about 60 to about 350° C., and outlet temperature is set from about 40 to about 210° C.

25. A controlled release tablet comprising a compressed blend of at least two dry powders, including a powder of at least one pharmaceutical agent and a powder of a controlled release excipient;
  wherein said controlled release excipient comprises a chemically-modified, cross-linked high amylose starch prepared by a method comprising:
  (a) cross-linking high amylose starch, followed by
  (b) chemically modifying the cross-linked high amylose starch, followed by
  (c) gelatinization, and
  (d) drying to obtain a powder of said controlled release excipient;
wherein said cross-linked high amylose starch is characterized in that upon solubilization in 90% DMSO at 80° C. for about three days and gel permeation chromatography, the height of the peak corresponding to amylose in said cross-linked high amylose starch is at least 90% of that of the peak corresponding to amylose in said high amylose starch prior to (a).

26. A controlled release tablet comprising a compressed blend of at least two dry powders, including a powder of at least one pharmaceutical agent and a powder of a controlled release excipient;
  wherein said controlled release excipient comprises a chemically-modified, cross-linked high amylose starch prepared by a method comprising:
  (a) cross-linking high amylose starch, followed by
  (b) chemically modifying the cross-linked high amylose starch, followed by
  (c) gelatinization, and
  (d) drying to obtain a powder of said controlled release excipient;
wherein said cross-linked high amylose starch is characterized in that less than about 20% of the amylose present in said high amylose starch prior to (a) is chemically cross-linked to amylopectin.

27. A controlled release tablet comprising a compressed blend of at least two dry powders, including a powder of at least one pharmaceutical agent and a powder of a controlled release excipient;
  wherein said controlled release excipient comprises a chemically-modified, cross-linked high amylose starch prepared by a method comprising:
  (a) cross-linking high amylose starch, followed by
  (b) chemically modifying the cross-linked high amylose starch, followed by
  (c) gelatinization, and
  (d) drying to obtain a powder of said controlled release excipient;
wherein said cross-linked high amylose starch is characterized in that upon solubilization in 90% DMSO at 80° C. for about three days and gel permeation chromatography, less than about 20% of the amylose present prior to (a) is chemically cross-linked to and eluted with amylopectin.

28. A controlled release tablet comprising a compressed blend of at least two dry powders, including a powder of at least one pharmaceutical agent and a powder of a controlled release excipient;
  wherein said controlled release excipient comprises a chemically-modified, cross-linked high amylose starch prepared by a method comprising:
  (a) cross-linking high amylose starch, followed by
  (b) chemically modifying the cross-linked high amylose starch, followed by
  (c) gelatinization, and
  (d) drying to obtain a powder of said controlled release excipient;
wherein said cross-linked high amylose starch is characterized in that upon solubilization in 90% DMSO at 80° C. for about three days and gel permeation chromatography, the height of the peak corresponding to amylose is higher than that of the peak corresponding to amylopectin-containing entities.

29. The tablet of claim 25, wherein said tablet is for oral administration.

30. The tablet of claim 25, wherein said tablet is an implant.

31. The tablet of claim 25, wherein said controlled release excipient comprises cross-linked high amylose starch prepared by cross-linking said high amylose starch and by a chemical modification selected from the group consisting of esterification and etherification.

32. The tablet of claim 31, wherein said chemical modification is hydroxypropylation.

33. The tablet of claim 32, wherein said cross-linked high amylose starch is hydroxypropylated with propylene oxide.

34. The tablet of claim 25, wherein said high amylose starch is cross-linked with a reagent selected from the group consisting of epichlorohydrin, adipic acid anhydride, sodium trimetaphosphate and phosphorous oxychloride.

35. The tablet of claim 25, wherein said cross-linked high amylose starch is gelatinized at a temperature of about 80° C. to about 180° C.

36. The tablet of claim 25, wherein said blend of dry powders comprises a lubricant and a filler.

37. The tablet of claim 36, wherein said lubricant is magnesium stearate.

38. The tablet of claim 37, where said filler is lactose.

39. The tablet of claim 25, wherein said pharmaceutical agent is pseudoephedrine hydrochloride, acetaminophen, diclofenac sodium, verapamil, glipizide, nifedipine, felodipine, betahistine, albuterol, acrivastine, omeprazole, misoprostol, tramadol, ciprofloxacin, oxybutynin, trimebutine, ketoconazole, acetylsalicylic acid, ibuprofen, ketoprofen, indomethacin, diflunisol, naproxen, ketorolac, diclofenac, tolmetin, sulindac, phenacetin, piroxicam, mefamanic acid, dextromethorphan, salicylates, pharmaceutically acceptable salts thereof or mixtures thereof.

40. A chemically-modified, cross-linked high amylose starch prepared by a method comprising:
  (a) cross-linking high amylose starch, followed by
  (b) chemically modifying the cross-linked high amylose starch, followed by
  (c) gelatinization, and
  (d) drying to obtain a powder of said controlled release excipient;
wherein said cross-linked high amylose starch is characterized in that upon solubilization in 90% DMSO at 80° C. for about three days and gel permeation chromatography, the height of the peak corresponding to amylose in said cross-linked high amylose starch is at least 90% of that of the peak corresponding to amylose in said high amylose starch prior to (a).

41. A chemically-modified, cross-linked high amylose starch prepared by a method comprising:
  (a) cross-linking high amylose starch, followed by
  (b) chemically modifying the cross-linked high amylose starch, followed by
  (c) gelatinization, and
  (d) drying to obtain a powder of said controlled release excipient;

wherein said cross-linked high amylose starch is characterized in that less than about 20% of the amylose present in said high amylose starch prior to (a) is chemically cross-linked to amylopectin.

42. A chemically-modified, cross-linked high amylose starch prepared by a method comprising:

(a) cross-linking high amylose starch, followed by (b) chemically modifying the cross-linked high amylose starch, followed by (c) gelatinization, and (d) drying to obtain a powder of said controlled release excipient;

wherein said cross-linked high amylose starch is characterized in that upon solubilization in 90% DMSO at 80° C. for about three days and gel permeation chromatography, less than about 20% of the amylose present prior to (a) is chemically cross-linked to and eluted with amylopectin.

43. A chemically-modified, cross-linked high amylose starch prepared by a method comprising:

(a) cross-linking high amylose starch, followed by (b) chemically modifying the cross-linked high amylose starch, followed by (c) gelatinization, and (d) drying to obtain a powder of said controlled release excipient;

wherein said cross-linked high amylose starch is characterized in that upon solubilization in 90% DMSO at 80° C. for about three days and gel permeation chromatography, the height of the peak corresponding to amylose is higher than that of the peak corresponding to amylopectin-containing entities.

* * * * *